United States Patent
Gray et al.

(10) Patent No.: US 11,672,705 B2
(45) Date of Patent: *Jun. 13, 2023

(54) SYSTEM FOR TREATING THE HUMAN LENS WITH A LASER

(71) Applicant: Lensar, Inc., Orlando, FL (US)

(72) Inventors: Gary P. Gray, Orlando, FL (US); Rudolph W. Frey, Maitland, FL (US); Jerome R. Kuszak, Oak Park, IL (US)

(73) Assignee: Lensar, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/889,634

(22) Filed: Jun. 1, 2020

(65) Prior Publication Data

US 2021/0038432 A1 Feb. 11, 2021

Related U.S. Application Data

(60) Continuation of application No. 15/404,116, filed on Jan. 11, 2017, now Pat. No. 10,667,950, which is a division of application No. 12/217,285, filed on Jul. 2, 2008, now Pat. No. 9,545,338, which is a continuation-in-part of application No. PCT/US2007/001353, filed on Jan. 19, 2007, which is a continuation-in-part of application No. 11/414,838, filed on May 1, 2006, now Pat. No. 8,262,646, and a continuation of application No. 11/414,819, filed on May 1, 2006, now Pat. No. 9,180,051, said application No. 11/414,838 is a continuation-in-part of application No. 11/337,127, filed on Jan. 20, 2006, now Pat. No. 10,842,675, said application No. 11/414,819 is a continuation-in-part of application No. 11/337,127, filed on Jan. 20, 2006, now Pat. No. 10,842,675.

(51) Int. Cl.
*A61F 9/00* (2006.01)
*A61F 9/008* (2006.01)

(52) U.S. Cl.
CPC .......... *A61F 9/00838* (2013.01); *A61F 9/008* (2013.01); *A61F 9/00827* (2013.01); *A61F 2009/0087* (2013.01); *A61F 2009/00887* (2013.01); *A61F 2009/00897* (2013.01)

(58) Field of Classification Search
CPC ............................ A61F 9/00838; A61F 9/008
USPC ........................................................ 606/4
See application file for complete search history.

(56) References Cited

U.S. PATENT DOCUMENTS

| | | | |
|---|---|---|---|
| 8,262,646 B2 * | 9/2012 | Frey | A61F 9/00827 606/4 |
| 8,801,186 B2 * | 8/2014 | Frey | A61B 3/14 351/221 |
| 2014/0121652 A1 * | 5/2014 | Myers | A61F 9/008 606/4 |

* cited by examiner

*Primary Examiner* — Nicole F Lavert
*Assistant Examiner* — Nicole F. Johnson
(74) *Attorney, Agent, or Firm* — Glen P. Belvis; Belvis Law, LLC.

(57) ABSTRACT

A system and method for increasing the amplitude of accommodation and/or changing the refractive power of lens material of a natural crystalline lens is provided. Generally, there is provided methods and systems for delivering a laser beam to a lens of an eye in a plurality of patterns results in the increased accommodative amplitude and/or refractive power of the lens. There is further provided a system and method of treating presbyopia by increasing both the flexibility of the human lens and the depth of field of the eye.

20 Claims, 29 Drawing Sheets

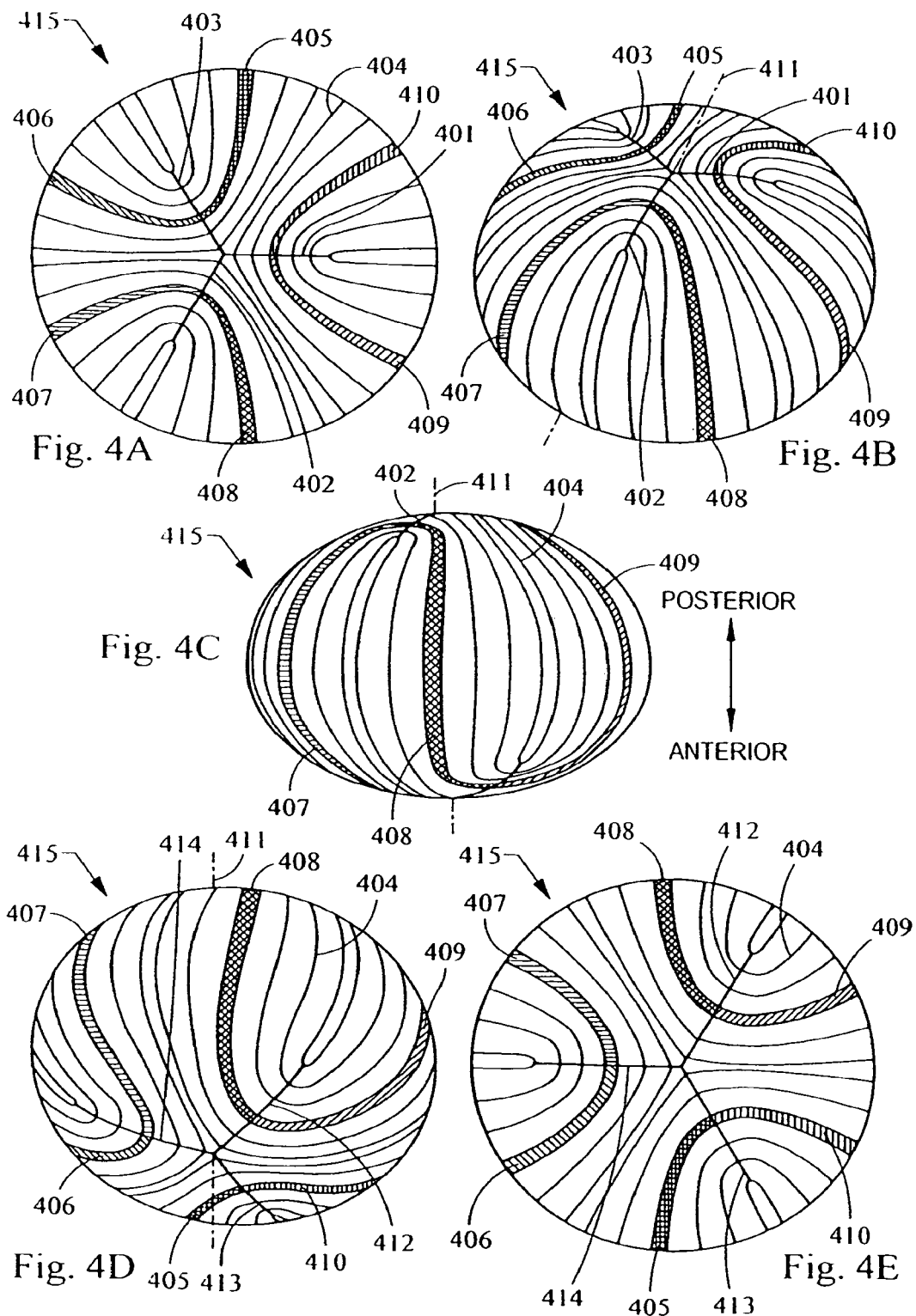

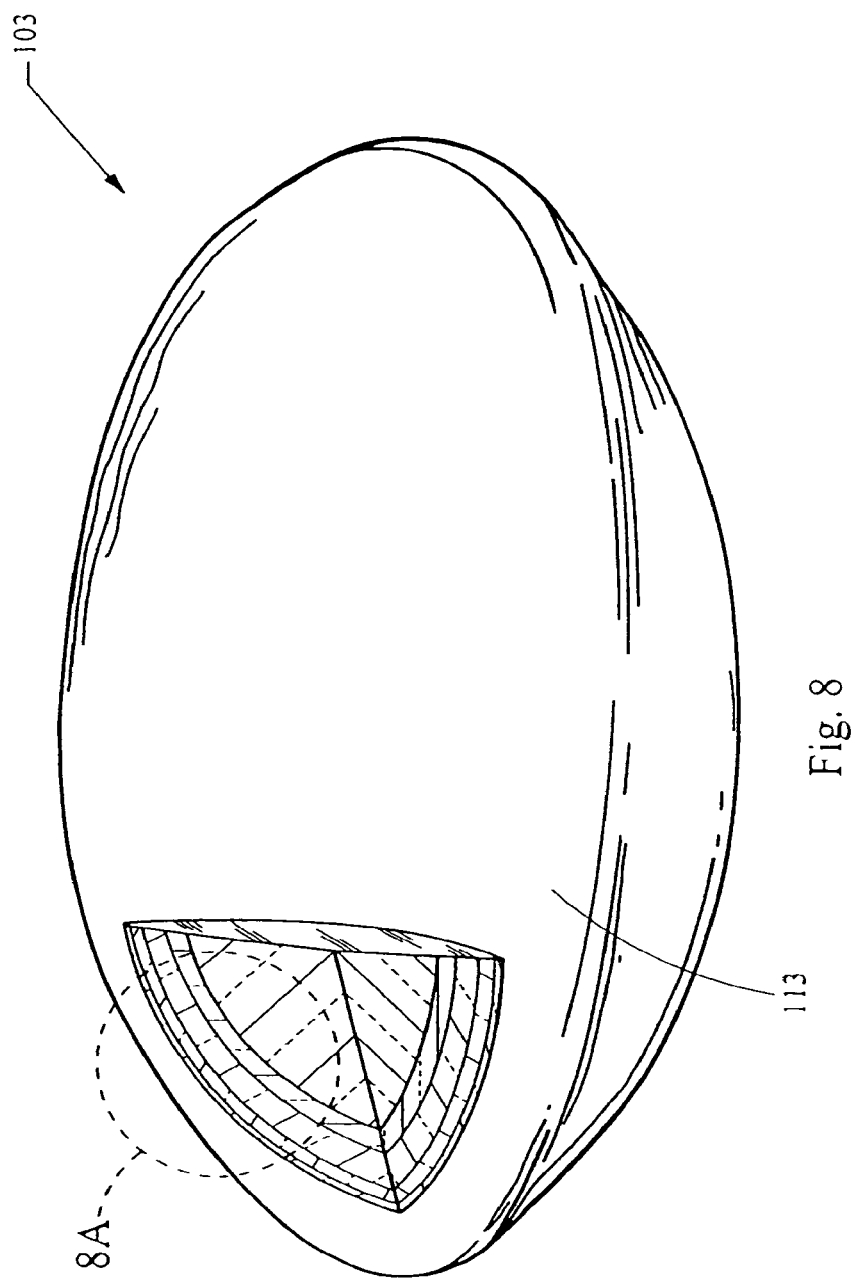

SYSTEM FOR TREATING THE HUMAN LENS WITH A LASER

This patent application is a continuation of Ser. No. 15/404,116 filed Jan. 11, 2017 (now U.S. Pat. No. 10,667, 950), which is a divisional of Ser. No. 12/217,285 filed Jul. 2, 2008 (now U.S. Pat. No. 9,545,338), which claims, under 35 U.S.C. §§ 120 and 365, the benefit of priority of the filing date of Jan. 19, 2007 of a Patent Cooperation Treaty patent application Serial Number PCT/US07/001353 (published as WO 2007/084627), filed on the aforementioned date, the entire contents of which are incorporated herein by reference, wherein Patent Cooperation Treaty patent application Serial Number PCT/US07/001353 is a continuation-in-part of application Frey et al. Ser. No. 11/414,838 filed on May 1, 2006 (now U.S. Pat. No. 8,262,646), and a continuation-in-part of Frey et al. Ser. No. 11/414,819 filed May 1, 2006 (now U.S. Pat. No. 9,180,051), which are both continuation-in-parts of application Frey et al. Ser. No. 11/337,127 filed Jan. 20, 2006 (now U.S. Pat. No. 10,842,675), the disclosures of each of the above mentioned applications are incorporated herein by reference.

BACKGROUND OF THE INVENTION

The present invention relates to systems and methods for treating the structure of the natural human crystalline lens with a laser to address a variety of medical conditions such as presbyopia, refractive error and cataracts and combinations of these.

The anatomical structures of the eye are shown in general in FIG. 1, which is a cross sectional view of the eye. The sclera 131 is the white tissue that surrounds the lens 103 except at the cornea 101. The cornea 101 is the transparent tissue that comprises the exterior surface of the eye through which light first enters the eye. The iris 102 is a colored, contractible membrane that controls the amount of light entering the eye by changing the size of the circular aperture at its center (the pupil). The ocular or natural crystalline lens 103, a more detailed picture of which is shown in FIGS. 1A-F, (utilizing similar reference numbers for similar structures) is located just posterior to the iris 102. The terms ocular lens, natural crystalline lens, natural lens, natural human crystalline lens, and lens (when referring to the prior terms) are used interchangeably herein and refer to the same anatomical structure of the human eye.

Generally, the ocular lens changes shape through the action of the ciliary muscle 108 to allow for focusing of a visual image. A neural feedback mechanism from the brain allows the ciliary muscle 108, acting through the attachment of the zonules 111, to change the shape of the ocular lens. Generally, sight occurs when light enters the eye through the cornea 101 and pupil, then proceeds through the ocular lens 103 through the vitreous 110 along the visual axis 104, strikes the retina 105 at the back of the eye, forming an image at the macula 106 that is transferred by the optic nerve 107 to the brain. The space between the cornea 101 and the retina 105 is filled with a liquid called the aqueous 117 in the anterior chamber 109 and the vitreous 110, a gel-like clear substance, in the chamber posterior to the lens 103.

FIG. 1A illustrates, in general, components of and related to the lens 103 for a typical 50-year old individual. The lens 103 is a multi-structural system. The lens 103 structure includes a cortex 113, and a nucleus 129, and a lens capsule 114. The capsule 114 is an outer membrane that envelopes the other interior structures of the lens. The lens epithelium 123 forms at the lens equatorial 121 generating ribbon-like cells or fibrils that grow anteriorly and posteriorly around the ocular lens. The nucleus 129 is formed from successive additions of the cortex 113 to the nuclear regions. The continuum of layers in the lens, including the nucleus 129, can be characterized into several layers, nuclei or nuclear regions. These layers include an embryonic nucleus 122, a fetal nucleus 130, both of which develop in the womb, an infantile nucleus 124, which develops from birth through four years for an average of about three years, an adolescent nucleus 126, which develops from about four years until puberty, which averages about 12 years, and the adult nucleus 128, which develops at about 18 years and beyond.

The embryonic nucleus 122 is about 0.5 mm in equatorial diameter (width) and 0.425 mm in Anterior-Posterior axis 104 (AP axis) diameter (thickness). The fetal nucleus 130 is about 6.0 mm in equatorial diameter and 3.0 mm in AP axis 104 diameter. The infantile nucleus 124 is about 7.2 mm in equatorial diameter and 3.6 mm in AP axis 104 diameter. The adolescent nucleus 126 is about 9.0 mm in equatorial diameter and 4.5 mm in AP axis 104 diameter. The adult nucleus 128 at about age 36 is about 9.6 mm in equatorial diameter and 4.8 mm in AP axis 104 diameter. These are all average values for a typical adult human lens approximately age 50 in the accommodated state, ex vivo. Thus, this lens (nucleus and cortex) is about 9.8 mm in equatorial diameter and 4.9 mm in AP axis 104 diameter. Thus, the structure of the lens is layered or nested, with the oldest layers and oldest cells towards the center.

The lens is a biconvex shape as shown in FIGS. 1 and 1A. The anterior and posterior sides of the lens have different curvatures, and the cortex and the different nuclei in general follow those curvatures. Thus, the lens can be viewed as essentially a stratified structure that is asymmetrical along the equatorial axis and consisting of long crescent fiber cells arranged end-to-end to form essentially concentric or nested shells. The ends of these cells align to form suture lines in the central and paracentral areas both anteriorly and posteriorly. The older tissue in both the cortex and nucleus has reduced cellular function, having lost their cell nuclei and other organelles several months after cell formation.

Compaction of the lens occurs with aging. The number of lens fibers that grow each year is relatively constant throughout life. However, the size of the lens does not become as large as expected from new fiber growth. The lens grows from birth through age 3, from 6 mm to 7.2 mm or 20% growth in only 3 years. Then, in the next approximate decade, growth is from 7.2 mm to 9 mm or 25%; however, this is over a 3 times longer period of 9 years. Over the next approximate two decades, from age 12 to age 36, the lens grows from 9 mm to 9.6 mm or 6.7% growth in 24 years, showing a dramatically slowing observed growth rate, while we believe there is a relatively constant rate of fiber growth during this period. Finally, in the last approximately 2 decades described, from age 36 to age 54, the lens grows by a tiny fraction of its youthful growth, from 9.6 to 9.8 mm or 2.1% in 18 years. Although there is a geometry effect of needing more lens fibers to fill larger outer shells, the size of the older lens is considerably smaller than predicted by fiber growth rate models, which consider geometry effects. Fiber compaction including nuclear fiber compaction is thought to explain these observations.

In general, presbyopia is the loss of accommodative amplitude. In general, refractive error is typically due to variations in the axial length of the eye. Myopia is when the eye is too long resulting in the focus falling in front of the retina. Hyperopia is when the eye is too short resulting in the focus falling behind the retina. In general, cataracts are areas of opacification of the ocular lens which are sufficient to interfere with vision. Other conditions, for which the present invention is directed, include but are not limited to the opacification of the ocular lens.

Presbyopia most often presents as a near vision deficiency, the inability to read small print, especially in dim lighting after about 40-45 years of age. Presbyopia, or the loss of accommodative amplitude with age, relates to the eye's inability to change the shape of the natural crystalline lens, which allows a person to change focus between far and near, and occurs in essentially 100% of the population. Accommodative amplitude has been shown to decline with age steadily through the fifth decade of life.

Historically, studies have generally attributed loss of accommodation to the hardening of the crystalline lens with age and more specifically, to an increase in the Young's Modulus of Elasticity of the lens material. More recent studies have examined the effect of aging on the relative change in material properties between the nucleus and cortex. These studies have provided varying theories and data with respect to the hardening of the lens. In general, such studies have essentially proposed the theory that the loss of flexibility is the result of an increase in the Young's Modulus of Elasticity of the nucleus and/or cortex material. Such studies have viewed this hardening as the primary factor in the loss of accommodative amplitude with age and hence the cause of presbyopia.

Although the invention is not bound by it, the present specification postulates a different theory of how this loss of lens flexibility occurs to cause presbyopia. In general, it is postulated that the structure of the lens, rather than the material properties of the lens, plays a greater role in loss of flexibility and resultant presbyopia than was previously understood. Thus, contrary to the teachings of the prior studies in this field as set forth above, material elasticity is not the dominate cause of presbyopia. Rather, it is postulated that the structure of the lens and changes in that structure with age are the dominant cause of presbyopia. Thus, without being limited to or bound by this theory, the present invention discloses a variety of methods and systems to provide laser treatments to increase the flexibility of the lens, based at least in part on the structure of the lens and structural changes that occur to the lens with aging. The present invention further discloses providing laser treatments to increase the flexibility of the lens that are based primarily on the structure of the lens and structural changes that occur to the lens with aging.

Accordingly, the postulated theory of this specification can be illustrated for exemplary purposes by looking to and examining a simple hypothetical model. It further being understood this hypothetical model is merely to illustrate the present theory and not to predict how a lens will react to laser pulses, and/or structural changes. To understand how important structure alone can be, consider a very thin plank of wood, say 4 ft by 4 ft square but 0.1 inch thick. This thin plank is not very strong and if held firmly on one end, it does not take much force to bend this thin plank considerably. Now consider five of these same 0.1 inch thickness planks stacked on top of each other, but otherwise not bound or tied together. The strength would increase and for the same force a somewhat smaller deflection will occur. Now, consider taking those same five planks and fastening them together with many screws or by using very strong glue, or by using many C-Clamps to bind them together. The strength of the bound planks is much higher and the deflection seen from the same force would be much smaller.

Without saying this simple model reflects the complex behavior of the lens, we generally hypothesize that when considering a volume of lens material, especially near the poles (AP axis), that is essentially bound by increased friction and compaction due to aging, that separating those bound layers into essentially unbound layers will increase the deflection of those layers for the same applied force and hence increase flexibility of the lens. Applicants, however, do not intend to be bound by the present theory, and it is provided solely to advance the art, and is not intended to and does not restrict or diminish the scope of the invention, Thus, further using this model for illustration purposes, under the prior theories and treatments for presbyopia, the direction was principally toward the material properties, i.e., Modulus of the material in the stack, rather than on the structure of the stack, i.e., whether the layers were bound together. On the other hand, the presently postulated theory is directed toward structural features and the effects that altering those features have on flexibility.

In general, current presbyopia treatments tend to be directed toward alternatives to increasing the amplitude of accommodation of the natural crystalline lens. These treatments include a new class of artificial accommodative Intraocular Lenses (IOL's), such as the Eyeonics CRYSTALENS, which are designed to change position within the eye; however, they offer only about 1 diopter of objectively measured accommodative amplitude, while many practitioners presently believe 3 or more diopters are required to restore normal visual function for near and far objects. Moreover, researchers are pursuing techniques and materials to refill the lens capsule with synthetic materials. Additionally, present surgical techniques to implant artificial accommodative IOL's are those developed for the more serious condition of cataracts. It is believed that practitioners are reluctant at the present time to replace a patient's clear albeit presbyopic natural crystalline lens, with an accommodative IOL due to the risks of this invasive surgical technique on a patient who may simply wear reading glasses to correct the near vision deficiency. However, developments may offer greater levels of accommodative amplitude in implantable devices and refilling materials. To better utilize such device improvements and to increase the accommodative amplitude of existing implantable devices, improved surgical techniques are provided herein as a part of the present invention.

Refractive error, typically due to the length of the eye being too long (myopia) or too short (hyperopia) is another very common problem effecting about one-half of the population. Laser surgery on the cornea, as proposed by Trokel and L'Esperance and improved by Frey and others, does offer effective treatment of refractive errors but factors such as higher degrees of refractive error, especially in hyperopia, thin corneas or a changing refractive error with time, such as that brought on by presbyopia, limit the clinical use of laser corneal surgery for many.

Cataracts, or the condition when the natural crystalline lens becomes opaque and clouds vision, occurs in millions of people per year and are treated effectively with a surgical techniques such as ultrasonic phacoemulsification pioneered by Kelman 30 years ago. Although the techniques have been refined over the years, safety concerns from ocular trauma, especially to the corneal endothelium from the ultrasonic energy required to break up a hardened cataract is undesirable; especially for those with a compromised corneal endothelium, such as those with Fuchs Dystrophy. Moreover, the use of lasers in the treatment of cataracts has a further issue. Cataracts scatter light, including laser light and thus can prevent a laser treatment beam from having the desired tissue effect. Accordingly, as provided in detail in this specification improvements in the delivery of lasers to cataractous tissue are provided herein.

SUMMARY

Provided herein are embodiments of the present invention. Accordingly, there is provided a system and method for delivering a laser beam to a lens of an eye in a plurality of patterns, which system and method in general comprise providing a laser, providing an optical path for directing a laser beam from the laser to the lens of the eye, directing the laser beam in a first pattern on a first portion of the lens of the eye, the first pattern generally following the shape of the outer surface of the lens of the eye, directing the laser beam in a second pattern on a second portion of the lens of the eye, the second pattern having a pattern to cover a specific volume of the second portion of the lens of the eye and wherein the relationship of the first pattern to the second pattern being such that the first pattern is positioned within the lens closer to the lens outer surface than the second pattern; and, both the first and second patterns positioned within the lens of the eye such that they avoid the central portion of the lens of the eye. In this system and method the second pattern may be cubic, the first shot pattern may be a plurality of nested shells, the first shot pattern may comprises a plurality of nested shells that follows the anterior surface of the lens of the eye, or other combinations and of patterns disclosed and taught herein. These shot patterns may further be delivered to the lens of the eye in a random manner. These shot patterns may still further have a central area avoided wherein the central area avoided has a width of about 1 mm centered approximately on the optical axis of the lens, wherein the central area avoided has is cylindrical in shape and has a diameter greater than about 1 mm centered approximately around the optical axis of the lens, wherein the central area avoided has a width of about 1.5 mm centered approximately on the optical axis of the lens, wherein the central area avoided is cylindrical in shape and has a diameter greater than about 1.5 mm centered approximately around the optical axis of the lens, wherein the central area avoided has a width of about 0.2 mm to about 4 mm centered approximately on the optical axis of the lens, wherein the central area avoided is cylindrical in shape and has a diameter of about 0.2 mm to about 4 mm centered approximately around the optical axis of the lens, wherein the central area avoided is cylindrical in shape and has a diameter of about 0.2 mm to about 4 mm centered approximately around the optical axis of the lens, wherein the central area avoided has a diameter of about 0.5 mm to about 3 mm centered approximately around the optical axis of the lens, wherein the central area avoided is cylindrical in shape and has a diameter of about 2 mm centered approximately around the optical axis of the lens, and wherein the second pattern is different from the first pattern, as well as other variations provide in the detailed description. These shot patterns may further be delivered to the lens of the eye in a random manner.

There is also provided a system and method of increasing depth of field for human vision, which system and method in general comprise providing an aperture for the lens of an eye; the aperture being formed from material comprising an opacified annulus of human lens material. In the system and method the annulus may be about 100% opacified, about 90% opacified, about 50% to about 100% opacified, about 20% to about 100% opacified, and other amounts of opacification between and around these amounts as taught herein.

Further the method and system of increasing depth of field for human vision may in general comprise providing an annulus of opacified material within the lens of an eye with the annulus being positioned away from the outer surfaces of the lens by at least about 0.25 mm. In a further system and method the annulus creates an aperture having a diameter of about 2 mm, as well as other variations as provided in the detailed description.

Additionally, there is provided methods and systems for treating presbyopia by increasing both the flexibility of the human lens and the depth of field of the eye. Thus, there may be provided an aperture for the lens of an eye, the aperture being formed from material comprising an opacified annulus of human lens material, in conjunction with providing a laser shot pattern to increase the flexibility of the lens. Further and more detailed implementations of this method and system are provided in the detailed description. These shot patterns may further be delivered to the lens of the eye in a random manner.

Further provided herein is a system for creating an annulus of opacified material from the lens of an eye, which system in general comprises a laser, laser focusing optics for providing a laser shot, a scanner and a control system comprising a pattern for directing a plurality of laser shots in an annular pattern to a portion of the lens of the eye, so that the laser shots so directed are predetermined to opacify the lens material. In this system the annular pattern may have an inner diameter of from about 0.5 mm to about 3 mm, the annular pattern may be centered approximately on the optical axis of the eye, the laser shots may be predetermined to opacify the lens material to from about 20% to about 100% opacification, as well as, other variations as provided in the detailed description. These shot patterns may further be delivered to the lens of the eye in a random manner.

Moreover, there is provided a system and a method of using this system for treating presbyopia which in general comprise a laser and laser focusing optics for providing a laser shot, a scanner; and, a control system comprising a first pattern for directing a plurality of laser shots in an annular pattern to a portion of the lens of the eye; and, a second pattern for directly a plurality of laser shots to a portion of the lens of the eye, and wherein the laser shots so directed in the first pattern are predetermined to opacify the lens material and the laser shots so directed in the second pattern are predetermined to increase the flexibility of the lens. In this system and method the first and second patterns may be provided to the lens of the eye substantially simultaneously or simultaneously, the second pattern may provide a pattern of nested shells, and the second pattern may be predetermined to avoid placing any laser shots in the central portion of the lens. Further, the central area avoided may have a width of about 1 mm centered approximately on the optical axis of the lens, the central area avoided may be cylindrical in shape and have a diameter greater than about 1 mm centered approximately around the optical axis of the lens, the central area avoided may have a width of about 1.5 mm centered approximately on the optical axis of the lens, the central area avoided may be cylindrical in shape and have a diameter greater than about 1.5 mm centered approximately around the optical axis of the lens, the central area avoided may have a width of about 0.2 mm to about 4 mm centered approximately on the optical axis of the lens, the central area avoided may be cylindrical in shape and have a diameter of about 0.2 mm to about 4 mm centered approximately around the optical axis of the lens, the central area avoided may be cylindrical in shape and have a diameter of about 0.2 mm to about 4 mm centered approximately around the optical axis of the lens, the central area avoided may have a diameter of about 0.5 mm to about 3 mm centered approximately around the optical axis of the lens, the central area avoided may be cylindrical in shape and have a diameter of about 2 mm centered approximately around the optical axis of the lens, the annular pattern may have an inner diameter of from about 0.2 mm to about 4 mm, as well as, other variations as provided in the detailed description. These shot patterns may further be delivered to the lens of the eye in a random manner.

There is still further provided a method and system for treating presbyopia in general comprising providing a laser beam to a portion of the lens of an eye, the portion consisting essentially of denucleated material. Thus, this system may be comprised of a laser, laser focusing optics, a scanner, and, a control system comprising a pattern for directing a plurality of laser pulses from the laser in a pattern to a portion of the lens of the eye, said portion consisting essentially of denucleated material. Further provided is a method for treating presbyopia in general comprising providing a laser beam in a shot pattern to a portion of a lens of an eye, the lens having an organelle degradation region and an organelle free regions, the shot pattern consisting essentially of shots directed toward the organelle degradation and/or organelle free regions of the lens of the eye. Still further there is provided a system and method for treating presbyopia in general comprising providing a laser beam in a shot pattern to a portion of a lens of an eye the lens having an organelle free region the shot pattern consisting essentially of shots directed toward the organelle free region of the lens of the eye. These shot patterns may further be delivered to the lens of the eye in a random manner.

Also, there is provided a system and method for delivering laser bursts to a lens of an eye in a pattern, this system and method in general comprise a laser for providing laser pulses, laser optics, for providing a plurality of bursts of laser pulses, the bursts in the plurality of bursts comprising a plurality of individual laser pulses, a scanner, the scanner having a scan rate, and, a control system, the control system comprising a predetermined laser shot pattern for directing the laser to a portion of the lens of the eye, the shot pattern comprising a plurality of points, wherein the scan rate is such that at least a majority of the pulses in any one burst in said plurality of bursts is placed nearer to a point than to other points in the shot pattern.

Further, there is provided a system and method for delivering a laser beam to a lens of an eye while increasing the probability of achieving LIOB, as defined in the detailed description, and reducing the Rayleigh range effect in general comprising a laser for providing laser pulses, the energy density for the laser pulses being predetermined to be at or near LIOB threshold, laser optics, for providing a plurality of bursts of laser pulses, the bursts in the plurality of bursts comprising a plurality of individual laser pulses, a scanner, the scanner having a scan rate; and, a control system, the control system comprising a predetermined laser shot pattern for directing the laser to a portion of the lens of the eye, the shot pattern comprising a plurality of shots, wherein the number of pulses in a burst is at least great enough to provide at least a 90% chance of obtaining LIOB at a spot in the lens corresponding to a shot in the shot pattern. Yet further, there is provided a method and system for delivering laser bursts to a lens of an eye in a pattern comprising a laser for providing laser pulses, the laser pulses spaced apart by time $t_1$, as defined in the detailed description, laser optics, for providing a plurality of bursts of laser pulses, the bursts in the plurality of bursts comprising a plurality of individual laser pulses, the bursts being spaced apart by time $t_3$, as defined in the detailed description, a scanner, and, a control system, the control system comprising a predetermined laser shot pattern for directing the laser to a portion of the lens of the eye, the shot pattern comprising a plurality of shots. Moreover, it may be such that wherein time $t_1$ is about 5 nanoseconds to about 20 nanoseconds and time $t_3$ is about 5 μseconds to about 33 μ seconds and the scanner has a scan rate of about 30 kHz to about 200 kHz. These shot patterns may further be delivered to the lens of the eye in a random manner.

There is still further provided a system and a method for delivering a laser beam to a lens of an eye in a plurality of patterns in general comprising a laser, an optical path for directing a laser beam from the laser to the lens of the eye, and, a control system for at least directing the laser beam in a shot pattern in the lens of the eye, the pattern being arranged in the lens of the eye in a substantially random manner.

Further there is provided a system and a method for delivering a laser beam to a lens of an eye in a pattern in general comprising a laser, an optical path for directing a laser beam from the laser to the lens of the eye, the optical path having an F/# greater than or equal to about 1.5, a control system for at least directing the laser beam in a shot pattern in the lens of the eye, the pattern consisting essential of a pattern of shots arranged vertically. The F/# may in this system be greater or equal to about 2. Moreover, there is provided a system for delivering a laser beam to a lens of an eye in a pattern in general comprising, a laser, an optical path for directing a laser beam from the laser to the lens of the eye, the optical path proving a laser spot size of x a control system for at least directing the laser beam in a shot pattern in the lens of the eye, the pattern consisting essential of a pattern of shots arranged vertically, said shots in said vertical pattern being spaced apart by less than 3x.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

BRIEF DESCRIPTION OF THE DRAWINGS

FIGS. 4A, 4B, 4C, 4D and 4E are diagrams representing elevation views of the geometry used for the development of laser shot patterns based upon the structure of the fetal nucleus (three suture branch nucleus) as it is rotated from the posterior view 4A through and to the anterior view 4E.

FIGS. 8 and 8A are perspective cutout views of an adult lens representing the placement of essentially concentric shells in accordance with the teachings of the present invention.

DETAILED DESCRIPTION OF THE DRAWINGS AND THE PREFERRED EMBODIMENTS

Figure 2:
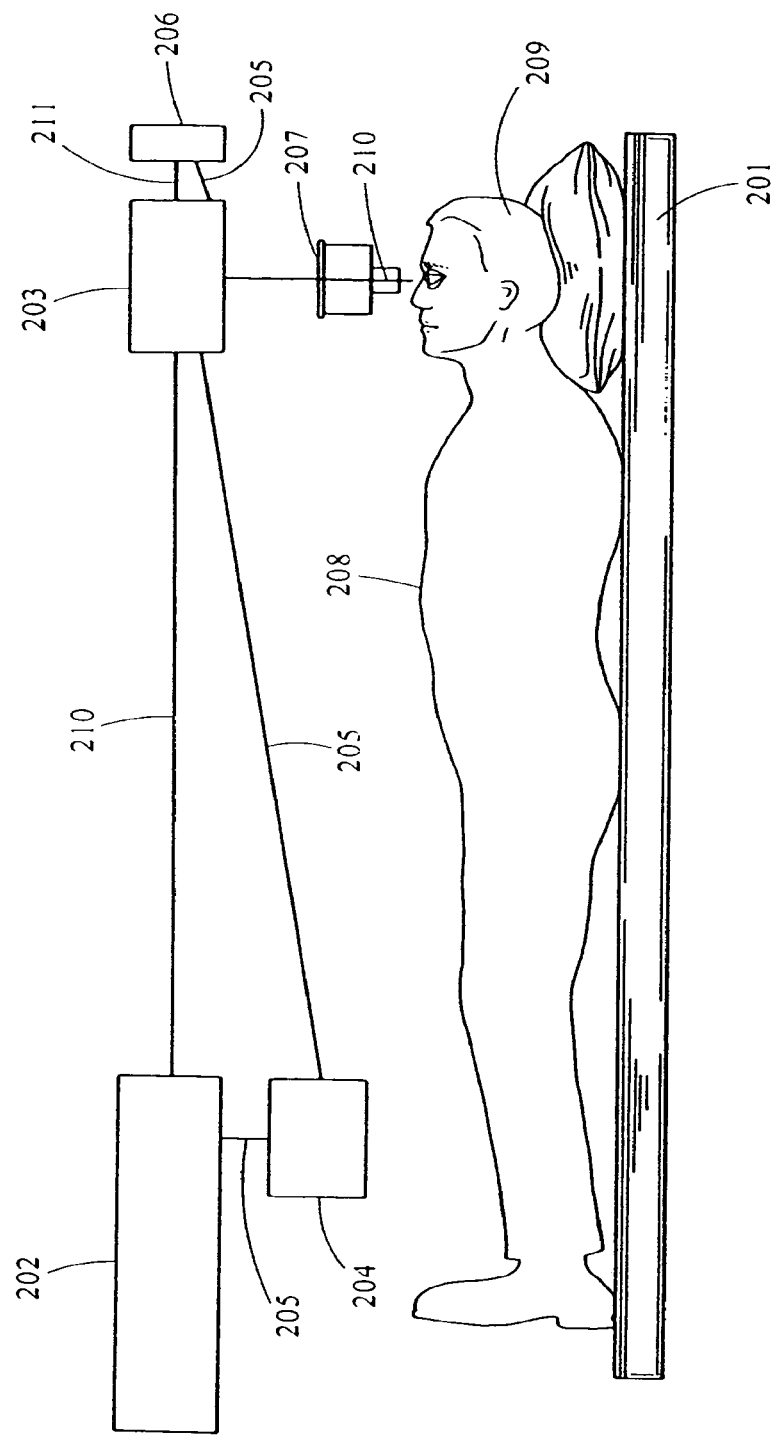
FIG. 2 is a block schematic diagram of a type of system for delivering a laser beam shot pattern to the lens of an eye according to the teachings of the present invention.

In general, the present invention provides a system and method for increasing the amplitude of accommodation and/or changing the refractive power and/or enabling the removal of the clear or cataractous lens material of a natural crystalline lens. Thus, as generally shown in FIG. 2 there is provided a system for delivering a laser beam shot pattern to the lens of an eye comprising: a patient support 201; a laser 202; optics for delivering the laser beam 203; a control system for delivering the laser beam to the lens in a particular pattern 204, which control system 204 is associated with and/or interfaces with the other components of the system as represented by lines 205; a means for determining the position of lens with respect to the laser 206, which means 206 receives an image 211 of the lens of the eye; and a laser patient interface 207.

The patient support 201 positions the patent's body 208 and head 209 to interface with the optics for delivering the laser beam 203.

In general, the laser 202 should provide a beam 210 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers would include: the Delmar Photonics Inc. Trestles-20, which is a Titanium Sapphire (Ti:Sapphire) oscillator having a wavelength range of 780 to 840 nm, less than a 20 femtosecond pulse width, about 100 MHz PRF, with 2.5 nanojoules; the Clark CPA-2161, which is an amplified Ti:Sapphire having a wavelength of 775 nm, less than a 150 femtosecond pulse width, about 3 KHz PRF, with 850 microjoules; the IMRA FCPA (fiber chirped pulse amplification) μJewel D series D-400-HR, which is a Yb:fiber oscillator/amplifier having a wavelength of 1045 nm, less than a 1 picosecond pulse width, about 5 MHz PRF, with 100 nanojoules; the Lumera Staccato, which is a Nd:YVO4 having a wavelength of 1064 nm, about 10 picosecond pulse width, about 100 KHz PRF, with 100 microjoules; the Lumera Rapid, which is a ND:YVO4 having a wavelength of 1064 nm, about 10 picosecond pulse width, and can include one or more amplifiers to achieve approximately 2.5 to 10 watts average power at a PRF of between 25 kHz to 650 kHz and also includes a multi-pulsing capability that can gate two separate 50 MHz pulse trains; and, the IMRA FCPA (fiber chirped pulse amplification) μJewel D series D-400-NC, which is a Yb:fiber oscillator/amplifier having a wavelength of 1045 nm, less than a 100 picosecond pulse width, about 200 KHz PRF, with 4 microjoules.

In general, the optics for delivering the laser beam 203 to the natural lens of the eye should be capable of providing a series of shots to the natural lens in a precise and predetermined pattern in the x, y and z dimension. The optics should also provide a predetermined beam spot size to cause photodisruption with the laser energy reaching the natural lens. Thus, the optics may include, without limitation: an x y scanner; a z focusing device; and, focusing optics. The focusing optics may be conventional focusing optics, and/or flat field optics and/or telecentric optics, each having corresponding computer controlled focusing, such that calibration in x, y, z dimensions is achieved. For example, an x y scanner may be a pair of closed loop galvanometers with position detector feedback. Examples of such x y scanners would be the Cambridge Technology Inc. Model 6450, the SCANLAB hurrySCAN and the AGRES Rhino Scanner. Examples of such z focusing devices would be the Phsyik International Peizo focus unit Model ESee Z focus control and the SCANLAB varrioSCAN.

In general, the control system for delivering the laser beam 204 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system as well as maintaining data, obtaining data and performing calculations. Thus, the control system may contain the programs that direct the laser through one or more laser shot patterns.

In general, the means for determining the position of the lens with respect to the laser 206 should be capable of determining the relative distance with respect to the laser and portions of the lens, which distance is maintained constant by the patient interface 207. Thus, this component will provide the ability to determine the position of the lens with respect to the scanning coordinates in all three dimensions. This may be accomplished by several methods and apparatus. For example, x y centration of the lens may be accomplished by observing the lens through a co-boresighed camera system and display or by using direct view optics and then manually positioning the patients' eye to a known center. The z position may then be determined by a range measurement device utilizing optical triangulation or laser and ccd system, such as the Micro-Epsilon opto NCDT 1401 laser sensor and/or the Aculux Laser Ranger LR2-22 . The use of a 3-dimensional viewing and measurement apparatus may also be used to determine the x, y and z positions of the lens. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera, which can view a reference and the natural lens, and would also include a light source to illuminate the natural lens. Such light source could be a structured light source, such as for example a slit illumination designed to generate 3-dimensional information based upon geometry.

A further component of the system is the laser patient interface 207. This interface should provide that the x, y, z position between the natural lens and the laser remains fixed during the procedure, which includes both the measurement steps of determining the x y z position and the delivery step of delivering the laser to the lens in a shot pattern. The interface device may contain an optically transparent applanator. One example of this interface is a suction ring applanator that is fixed against the outer surface of the eye and is then positioned against the laser optical housing, thus fixing the distance between the laser, the eye and the natural lens. The reference marks for the 3-dimensional viewing and measuring apparatus may also be placed on this applanator. A further example of a laser patient interface is a device having a lower ring, which has suction capability for affixing the interface to the eye. The interface further has a flat bottom, which presses against the eye flattening the eye's shape. This flat bottom is constructed of material that transmits the laser beam and also preferably, although not necessarily, transmits optical images of the eye within the visible light spectrum. The upper ring has a structure for engaging with the housing for the laser optics and/or some structure that is of known distance from the laser along the path of the laser beam and fixed with respect to the laser. The flat bottom further has a reference, which consists of three reference marks. Although three marks are provided in this example to make up the reference, the reference may consist of only a single mark or several marks. Further examples of such devices are generally disclosed in US D462442, US D462443, and US D459807S, the disclosures of which are hereby incorporated by reference. As an alternative to an applanator, the interface may be a corneal shaped transparent element whereby the cornea is put into direct contact with the interface or contains an interface fluid between.

Figure 2A:
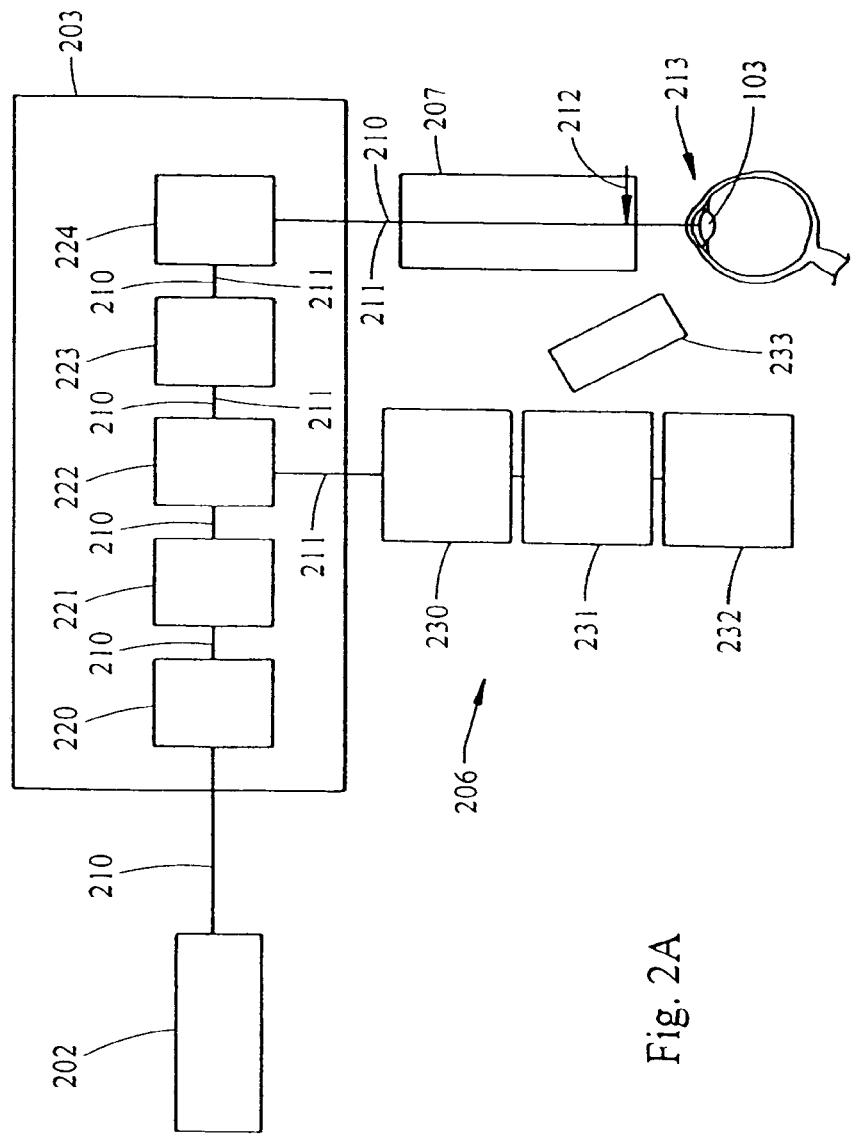
FIG. 2A is a block schematic diagram of illustrative components forming a portion of a system for delivering a laser beam shot pattern to the lens of an eye according to the teachings of the present invention.

An illustrative combination utilizing by way of example specific optics for delivering the laser beam 203 and means for determining the position of the lens 206, is shown in part, in FIG. 2A. FIG. 2A is a more detailed schematic diagram of a configuration of the system of FIG. 2. Thus, the example of FIG. 2A provides a laser 202, laser optics for delivering the laser beam 203, which optics comprise a beam expander telescope 220, a z focus mechanism 221, a beam combiner 222, an x y scanner 223, and focusing optics 224. There is further provided in FIG. 2A relay optics 230, camera optics with zoom and focus 231, and a ccd camera 232, which components form a part of a three-dimensional viewing and measuring apparatus. Moreover, these components 230, 231 and 232 in combination with a light source 233, the reference mark 212 and the scanner 223 function as a means for determining the position of the lens 206.

This combination of FIG. 2A utilizes the x y scanner 223 to create stereoscopic images of the lens with only a single ccd camera 232. Optical images 211 of the eye 213 and in particular optical images of the natural lens 103 of the eye 213 are conveyed along a path 211. This path 211 follows the same path as the laser beam 210 from the natural lens 103 through the laser patient interface 207, the focusing optics 224, the x y scanner 223 and the beam combiner 222. This combination of FIG. 2A further comprises: a laser patient interface 207, with a reference mark 212; and a light source 233, which could be for example uniform illumination, a slit illumination, or other structured light source designed to enhance 3-dimensional accuracy. The light source, in part, provides illumination of the natural lens of the patient's eye for the purposes of determining the 3-dimensional dimensional position of the lens. Thus, either stereoscopic images and/or the information from the camera are sent to a controller and/or computer (not shown in FIG. 2A) for further processing and use in determining 3-dimensional positions of the lens. Stereo images may be generated by commanding the scanner to go to and pause at a nominal left position and then electronically trigger the camera and controller to capture and store the left image; then command the scanner/camera/controller similarly to capture and store right image. This sequence may be repeated in a periodic manner. These left and right images can be processed by the controller to generate the position and shape of the lens. The left and right images can be displayed using a stereo video monitor. Camera images or stereo images may also be used to measure suture geometry and orientation in the patient's lens, which can be used to determine the parameters of suture based shot patterns and to align suture based shot patterns to the patient's lens suture geometry and orientation. The combination illustrated in FIG. 2A provides 3-dimensional information that can be used to determine the shape of the lens, including the anterior and posterior surfaces thereof. This information can also be used to visualize the structure of the lens, including sutures. Moreover, the information about the lens obtained from the combination of FIG. 2A can further be used in determining the laser shot pattern and laser shot placement with respect to lens shape and/or structure.

FIG. 2 and FIG. 2A are block schematic diagrams and thus the relative positions and spacing of the components illustrated therein are by way of example. Accordingly, the relative placements of these components with respect to one another may be varied and all or some of their functions and components may be combined.

Figure 1:
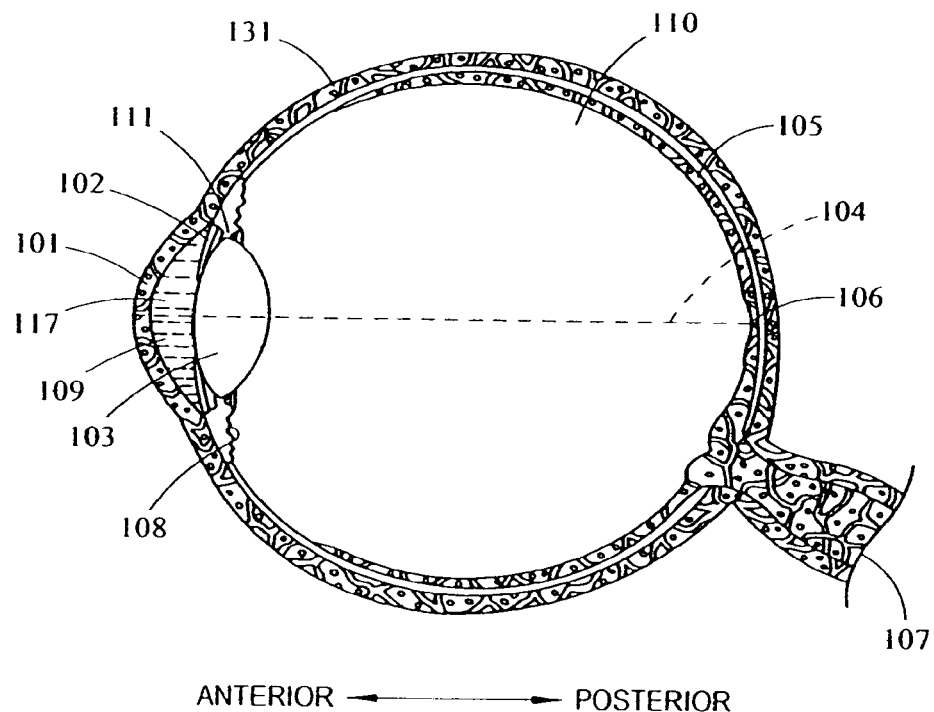
FIGS. 1 and 1A are cross sectional representations of the human eye.
Figure 1A:
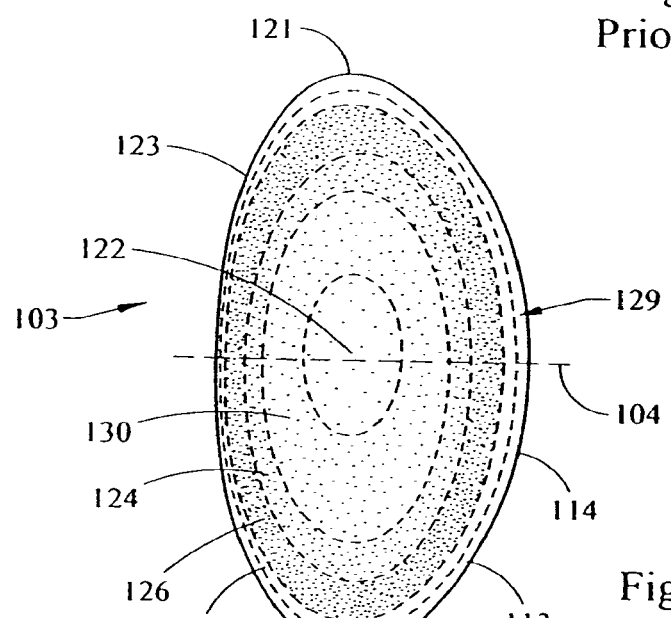

FIGS. 4A-E illustrate the three branched or Y suture geometry in the context of the structures found in the fetal nucleus 415 of the lens. Thus, these figures provide a more detailed view of the structures illustrated as layer 130, which encompasses layer 122 of FIG. 1A. In FIGS. 4 A-E the view of the inner layer of the lens is rotated stepwise from the posterior side FIG. 4A to the anterior side FIG. 4E of the lens. Thus, this layer of the lens has three posterior suture lines 401, 402, and 403. This layer also has three anterior suture lines 412, 413 and 414. The anterior suture lines are longer than the posterior suture lines and these lines are staggered when viewed along the anterior to posterior (AP) axis 411. The lens fibers, which form the layers of the nucleus, are shown by lines 404, it being understood that these are only illustrative lines and that in the actual natural layer of the lens there would be many times more fibers present. To aid in illustrating the structure and geometry of this layer of the nucleus representative fibers 405, 406, 407, 408, 409 and 410 have been exaggerated and individually shaded in FIGS. 4A-E. Thus, as the view of the lens nucleus is rotated from posterior to anterior the positions of these representative fibers, their relationship to each other, and their relationship to the suture lines is illustrated.

The length of the suture lines for the anterior side is approximately 75% of the equatorial radius of the layer or shell in which they are found. The length of the suture lines for the posterior side is approximately 85% of the length of the corresponding anterior sutures, i.e., 64% of the equatorial radius of that shell.

The term—essentially follows—as used herein would describe the relationship of the shapes of the outer surface of the lens and the fetal nucleus 415. The fetal nucleus is a biconvex shape. The anterior and posterior sides of the lens have different curvatures, with the anterior being flatter. These curvatures generally follow the curvature of the cortex and the outer layer and general shape of the lens. Thus, the lens can be viewed as a stratified structure consisting of long crescent fiber cells arranged end-to-end to form essentially concentric or nested shells.

As provided in greater detail in the following paragraphs and by way of the following examples, the present invention utilizes this and the further addressed geometry, structure and positioning of the lens layers, fibers and suture lines to provide laser shot patterns for increasing the accommodative amplitude of the lens. Although not being bound by this theory, it is presently believed that it is the structure, positioning and geometry of the lens and lens fibers, in contrast to the material properties of the lens and lens fibers, that gives rise to loss of accommodative amplitude. Thus, these patterns are designed to alter and affect that structure, positioning and/or geometry to increase accommodative amplitude.

Figure 5A:
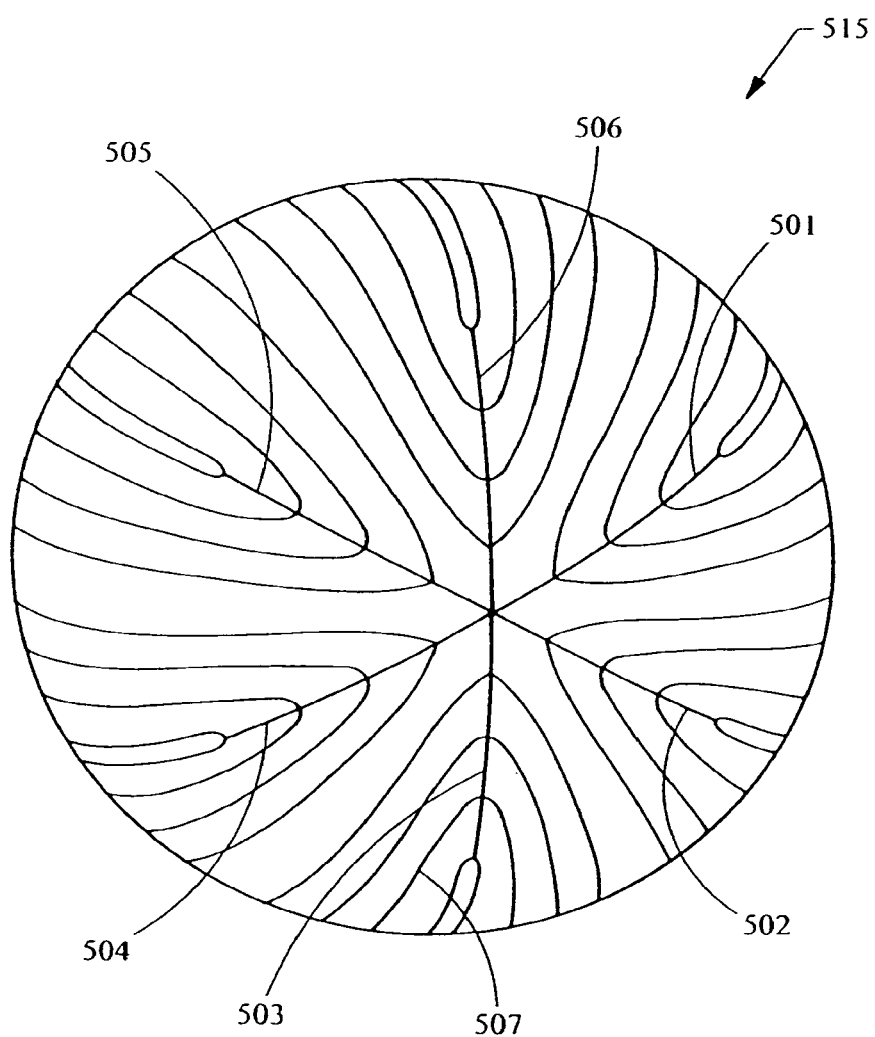
FIGS. 5A, 5B, and 5C are diagrams representing posterior, side and anterior elevation views, respectively, of the geometry used for the development of laser shot patterns based upon the structure of the infantile nucleus (six suture branch nucleus).
Figure 5B:
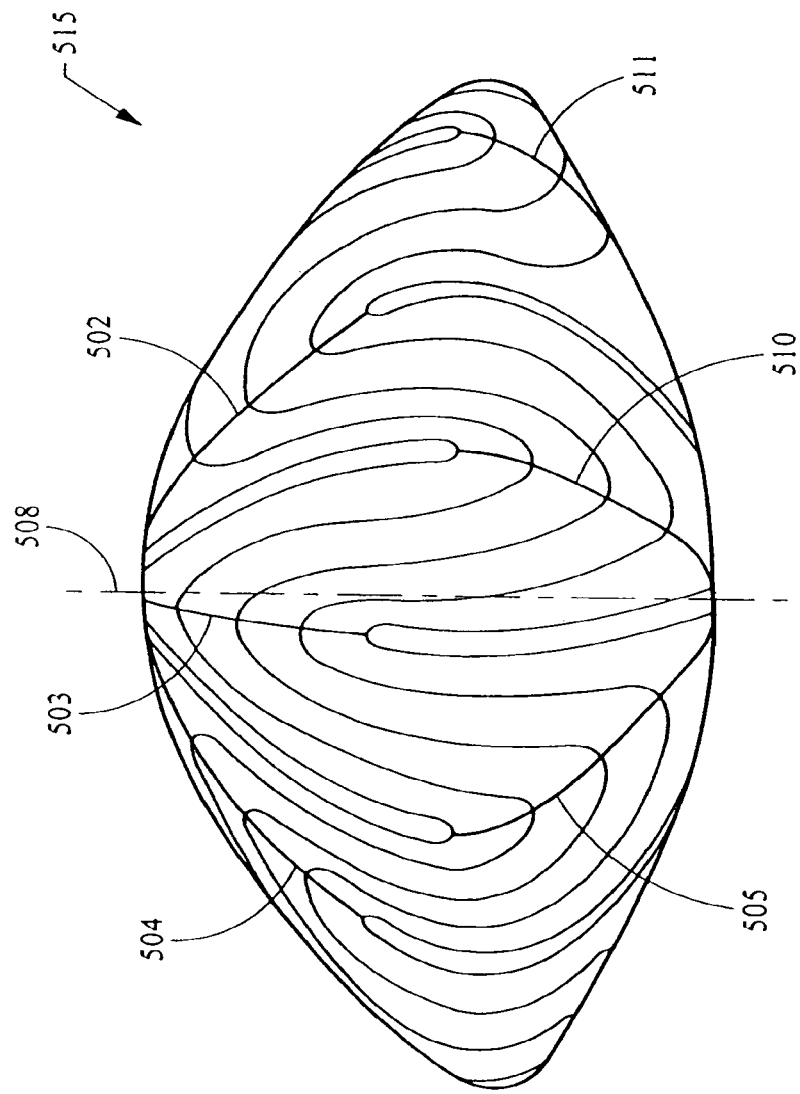
Figure 5C:
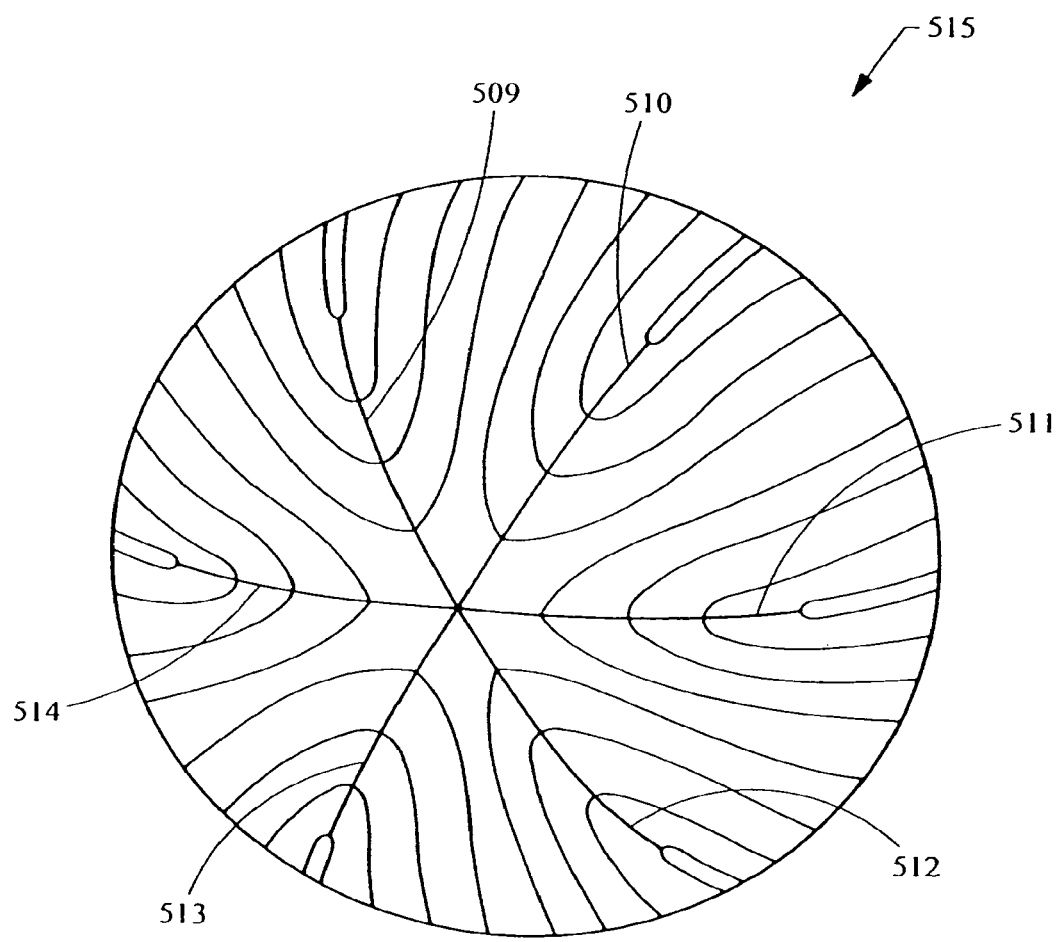

FIGS. 5A-C illustrates the six branched or star suture geometry in the context of the structure found in the infantile layer of the nucleus 515 of the lens. Thus, these figures provide a more detailed view of the structures illustrated as layer 124 of FIG. 1A. In FIGS. 5A-C the view of the layer of the lens is rotated from the posterior side FIG. 5A to a side view FIG. 56 to the anterior side FIG. 5C. Thus, this layer of the nucleus has six posterior suture lines 501, 502, 503, 504, 505, and 506. This layer of the nucleus also has six anterior suture lines 509, 510, 511, 512, 513, and 514. The anterior suture lines are longer than the posterior suture lines and these lines are staggered when viewed along the AP axis 508. The lens fibers, which form the layers of the nucleus, are shown by lines 507, it being understood that these are only illustrative lines and that in the actual natural layer of the lens there would be many times more fibers present.

The shape of the outer surface of the lens essentially follows the infantile nucleus 515, which is a biconvex shape. Thus, the anterior and posterior sides of this layer of the lens have different curvatures, with the anterior being flatter. These curvatures generally follow the curvature of the cortex and the outer layer and general shape of the lens. These curvatures also generally follow the curvature of the fetal nucleus 415. Thus, the lens can be viewed as a stratified structure consisting of long crescent fiber cells arranged end-to-end to form essentially concentric or nested shells, with the infantile nucleus 515 having the fetal nucleus 415 nested within it. As development continues through adolescence, additional fiber layers grow containing between 6 and 9 sutures.

Figure 6A:
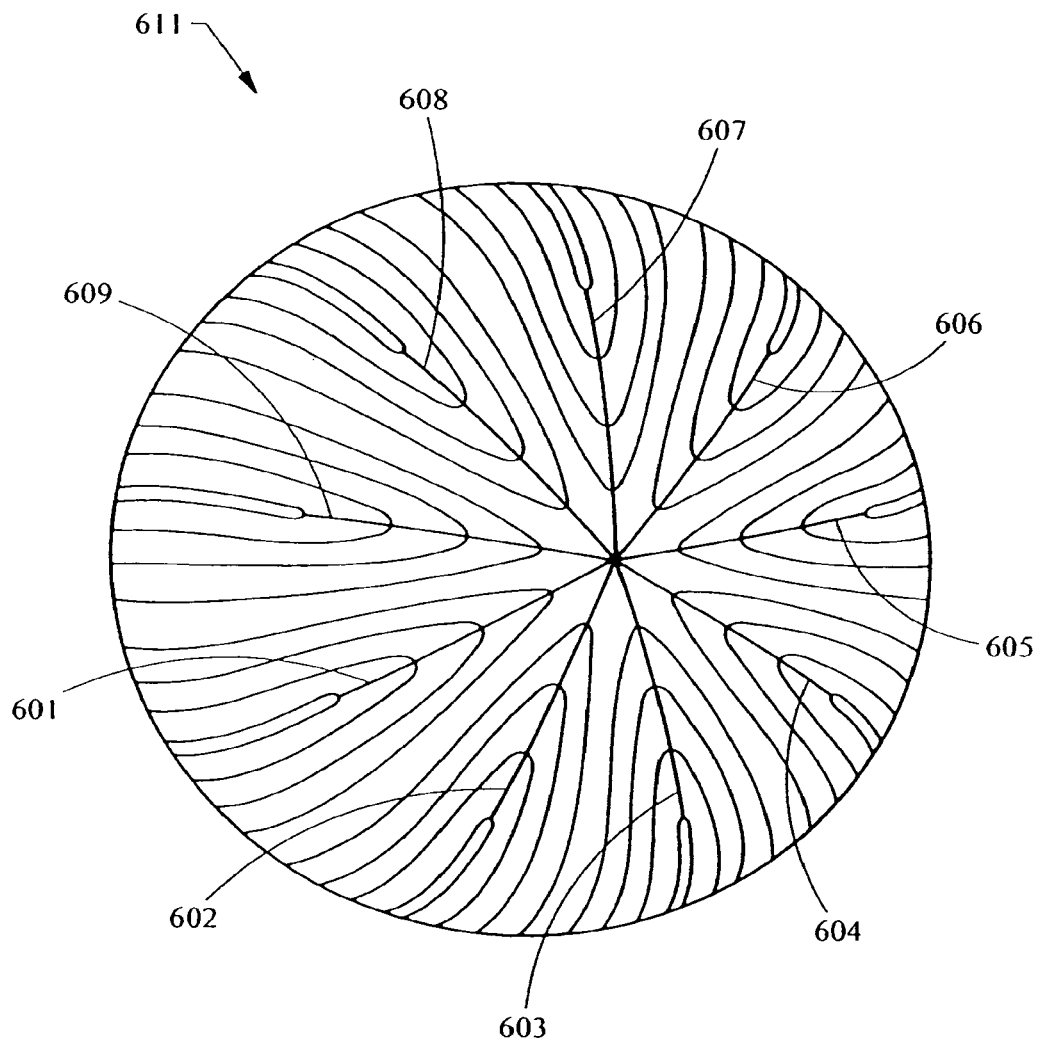
FIGS. 6A, 6B and 6C are diagrams representing posterior, side and anterior elevation views, respectively of the geometry used for the development of laser shot patterns based upon the structure of the adolescent nucleus (nine suture branch nucleus).
Figure 6B:
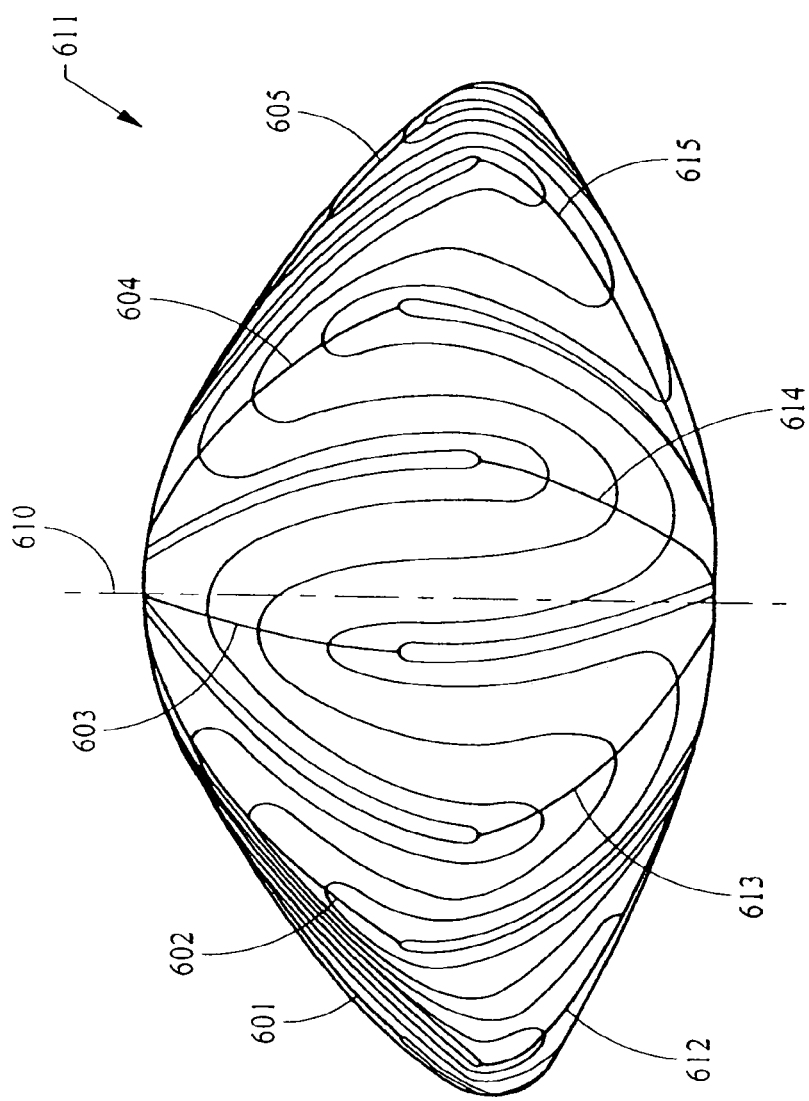
Figure 6C:
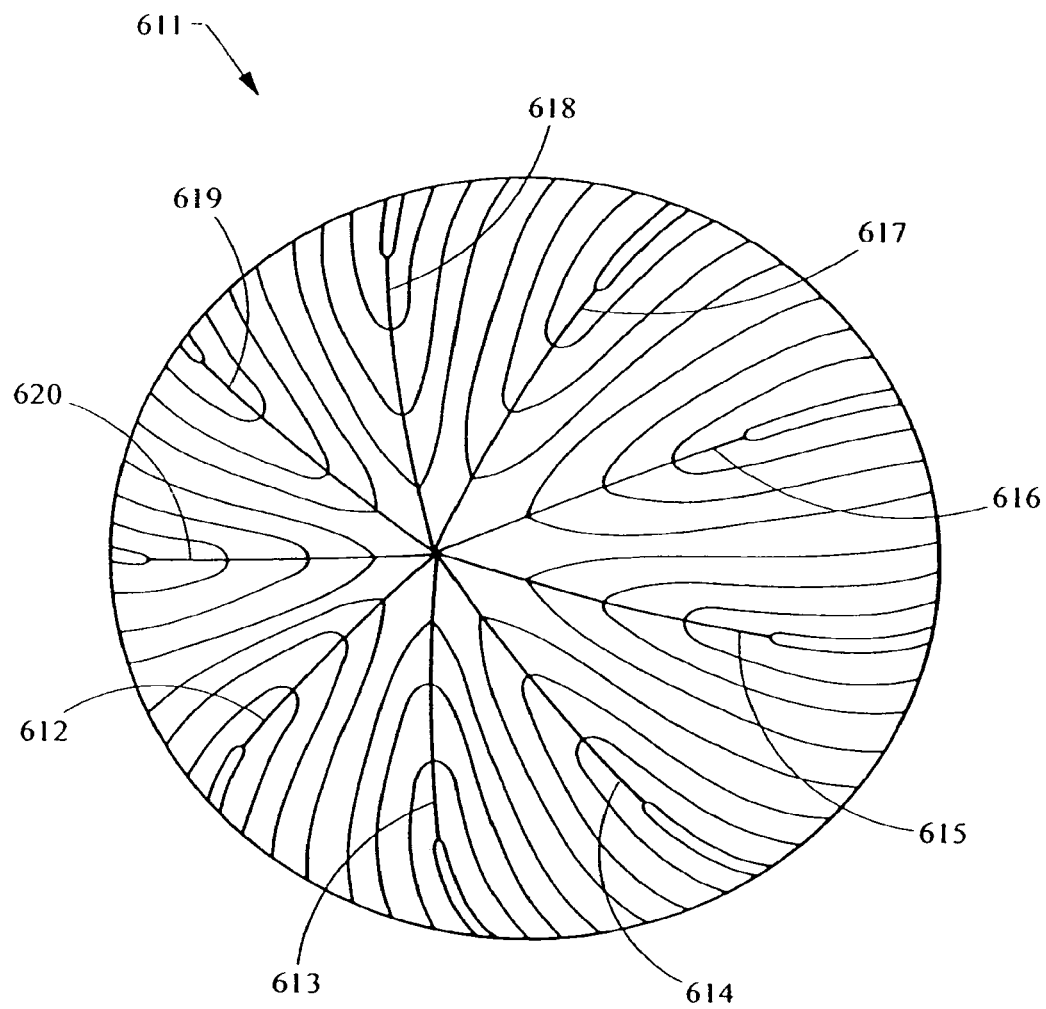

FIGS. 6A-C illustrates the nine branched or star suture geometry in the context of the structure found in the adolescent layer of the nucleus 611 of the lens. Thus, these figures provide a more detailed view of the structures illustrated as layer 126 of FIG. 1A. In FIGS. 6A-C the view of the layer of the lens is rotated from the posterior side FIG. 6A to a side view FIG. 6B to the anterior side FIG. 6C. Thus, this layer of the nucleus has nine posterior suture lines 601, 602, 603, 604, 605, 606, 607, 608 and 609. This layer of the nucleus also has nine anterior suture lines 612, 613, 614, 615, 616, 617, 618, 619 and 620. The anterior suture lines are longer than the posterior suture lines and these lines are staggered when viewed along the AP axis 610. The lens fibers, which form the layers of the nucleus, are shown by lines 621; it being understood that these are only illustrative lines, and that in the actual natural layer of the lens there would be many times more fibers present.

The outer surface of the cornea follows the adolescent nucleus 611, which is a biconvex shape. Thus, the anterior and posterior sides of this layer have different curvatures, with the anterior being flatter. These curvatures generally follow the curvature of the cortex and the outer layer and general shape of the lens. These curvatures also generally follow the curvature of the fetal nucleus 415 and the infantile nucleus 515, which are nested within the adolescent nucleus 611. Thus, the lens can be viewed as a stratified structure consisting of long crescent fiber cells arranged end-to-end to form essentially concentric or nested shells. As development continues through adulthood, additional fiber layers grow containing between 9 and 12 sutures.

Figure 7A:
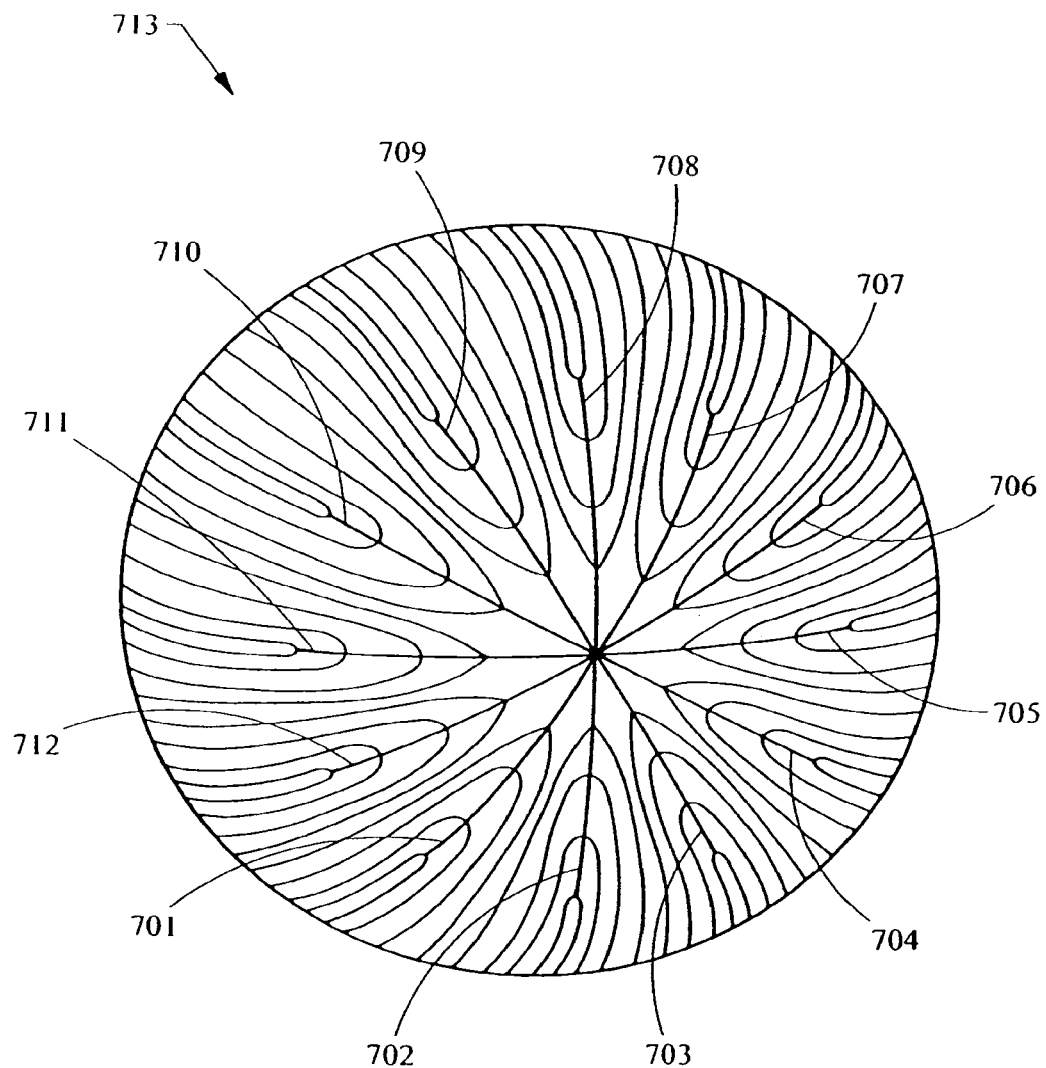
FIGS. 7A, 7B and 7C are diagrams representing posterior, side and anterior elevation views, respectively of the geometry used for the development of laser shot patterns based upon the structure of the an adult nucleus (12 suture branch).
Figure 7B:
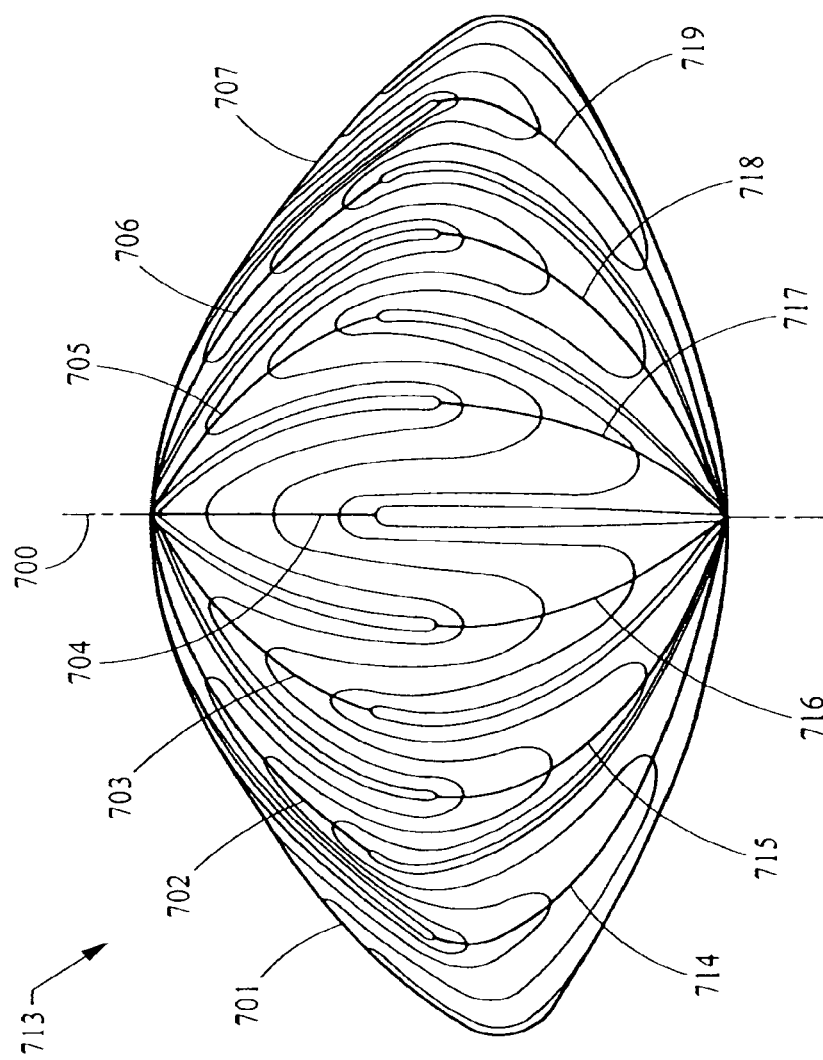
Figure 7C:
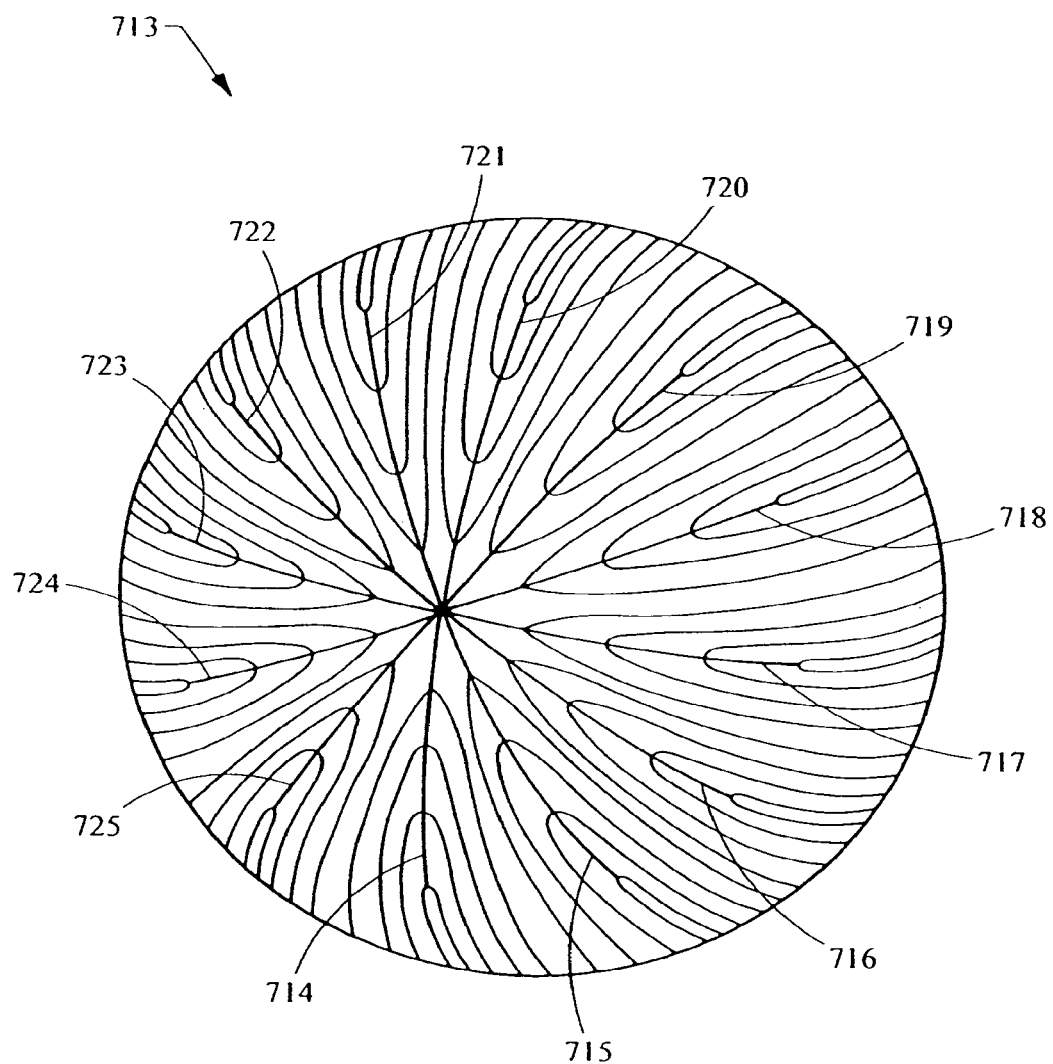

FIGS. 7A-C illustrate the twelve branched or star suture geometry in the context of the structure found in the adult layer of the nucleus 713 of the lens. Thus, these figures provide a more detailed view of the adult layer 128 depicted in FIG. 1A. In FIGS. 7A-C the view of the layer of the lens is rotated from the posterior side FIG. 7A to a side view FIG. 7B to the anterior side FIG. 7C. Thus, the adult layer of the nucleus has twelve posterior suture lines 701, 702, 703, 704, 705, 706, 707, 708, 709, 710, 711, and 712. This layer of the nucleus also has twelve anterior suture lines 714-725. The anterior suture lines are longer than the posterior suture lines and these lines are staggered when viewed along the AP axis 726. The lens fibers, which form the layers of the nucleus, are shown by lines 728; it being understood that these are only illustrative lines, and that in the actual natural layer of the lens there would be many times more fibers present.

The adult nucleus 713 is a biconvex shape that follows the outer surface of the lens. Thus, the anterior and posterior sides of this layer have different curvatures, with the anterior being flatter. These curvatures follow the curvature of the cortex and the outer layer and shape of the lens. These curvatures also generally follow the curvature of the adolescent nucleus 611, the infantile nucleus 515 and the fetal nucleus 415 and the embryonic nucleus, which are essentially concentric to and nested within the adult nucleus 611. Thus, the lens can be viewed as a stratified structure consisting of long crescent fiber cells arranged end to end to form essentially concentric or nested shells.

A subsequent adult layer having 15 sutures may also be present in some individuals after age 40. This subsequent adult layer would be similar to the later adult layer 713 in general structure, with the recognition that the subsequent adult layer would have a geometry having more sutures and would encompass the later adult layer 713; and as such, the subsequent adult layer would be the outermost layer of the nucleus and would thus be the layer further from the center of the nucleus and the layer that is youngest in age.

In general, the present invention provides for the delivery of the laser beam in patterns that utilize, or are based at least in part on, the lens suture geometry and/or the curvature of the lens and/or the various layers within the nucleus; and/or the curvatures of the various layers within the nucleus; and/or the suture geometry of the various layers within the nucleus. As part of the present invention the concept of matching the curvature of the anterior ablations to the specific curvature of the anterior capsule, while having a different curvature for posterior ablations, which in turn match the posterior curvature of the lens is provided. Anterior and posterior curvatures can be based on Kuszak aged lens models, Burd's numeric modeling, Burd et al. Vision Research 42 (2002) 2235-2251, or on specific lens measurements, such as those that can be obtained from the means for determining the position of the lens with respect to the laser. Thus, in general, these laser delivery patterns are based in whole and/or in part on the mathematical modeling and actual observation data regarding the shape of the lens, the shape of the layers of the lens, the suture pattern, and the position of the sutures and/or the geometry of the sutures.

Moreover, as set forth in greater detail, it is not necessary that the natural suture lines of the lens or the natural placement of the layers of the lens be exactly replicated in the lens by the laser shot pattern. In fact, exact replication of these natural structures by a laser shot pattern, while within the scope of the invention, is not required, and preferably is not necessary to achieve an increase in accommodative amplitude. Instead, the present invention, in part, seeks to generally emulate the natural lens geometry, structures and positioning and/or portions thereof, as well as build upon, modify and reposition such naturally occurring parameters through the use of the laser shot patterns described herein.

Figure 8A:
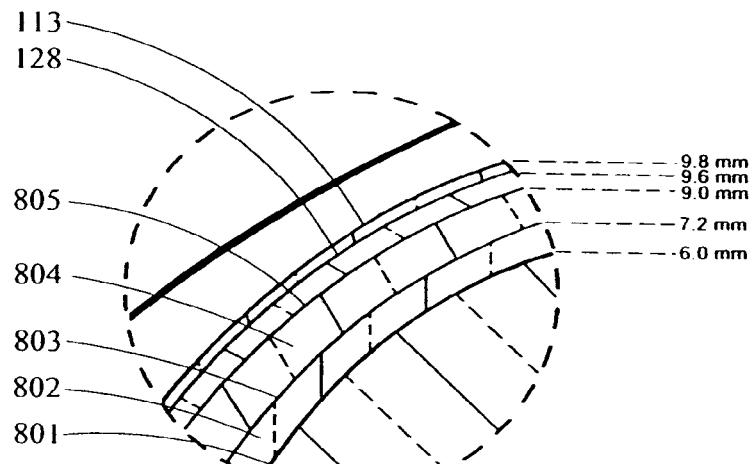

Accordingly, laser beam delivery patterns that cut a series of essentially concentric, i.e., nested, shells in the lens may be employed. Preferably, the shells would essentially follow the anterior and posterior curvature of the lens. Thus, creating in the lens a series of cuts which resemble the nucleus layers of FIGS. 4, 5, 6 and 7. These cuts may follow the same geometry, i.e., shape and distance from the center, of these layers or may follow only a part of that geometry. One example of these shells is illustrated in FIG. 8, which provides a lens 103, a first shell cut 801, a first shell 802, a second shell cut 803, a second shell 804 and a third shell cut 805. The adult nucleus 128 and cortex 113 are also provided. Thus, the term shell refers to the lens material and the term shell cut refers to the laser beam delivery pattern and consequently the placement of the laser beam shots in the lens in accordance with that pattern. More or less shell cuts, and thus shells may be utilized. Moreover, the cuts may be such that they in effect create a complete shell, i.e., the shell and shell cuts completely encompass a volume of lens material. The cuts may also be such that less than a complete shell is formed. Thus, the creation of partial shells, by the use of partial shell cuts, may be employed. Such partial cuts would for example be only a portion of a shell e.g., the anterior quartile, the anterior half, the posterior quartile, stacked annular rings, staggered annular rings, and/or combinations thereof. Such partial shells and shell cuts may be any portion of a three dimensional form, including ellipsoid, spheroids and combinations thereof as those terms are used in their broadest sense that in general follows the contours of the lens, capsule, cortex, nucleus, and/or the layers of the lens including the layers of the nucleus. Moreover, the use of complete and partial shells and shell cuts may be used in a single lens. Thus, by way of illustration of this latter point, the first and second cuts 801 and 803 are annular cuts, while the third cut is a complete cut.

A further use of partial shells is to have the shape of the shells follow the geometry and/or placement of the suture lines. Thus, partial pie shaped shells are created, by use of partial pie shaped shell cuts. These cuts may be placed in between the suture lines at the various layers of the lens. These partial shells may follow the contour of the lens, i.e., have a curved shape, or they may be flatter and have a more planar shape or be flat. A further use of these pie shape shells and shell cuts would be to create these cuts in a suture like manner, but not following the natural suture placement in the lens. Thus, a suture like pattern of cuts is made in the lens, following the general geometry of the natural lens suture lines, but not their exact position in the lens. In addition to pie shaped cuts other shaped cuts may be employed, such as by way of illustration a series of ellipses, rectangular planes or squares.

A further use of partial shells and/or planar partial shells is to create a series of overlapping staggered partial shells by using overlapping staggered partial shell cuts. In this way essentially complete and uninterrupted layers of lens material are disrupted creating planar like sections of the lens that can slide one atop the other to thus increase accommodative amplitude. These partial shells can be located directly atop each other, when viewed along the AP axis, or they could be slightly staggered, completely staggered, or any combination thereof.

In addition to the use of shells and partial shells, lines can also be cut into the lens. These lines can follow the geometry and/or geometry and position of the various natural suture lines. Thus, a laser shot pattern is provided that places shots in the geometry of one or more of the natural suture lines of one or more of the various natural layers of the lens as shown in FIGS. 4, 5, 6, and 7, as well as in the 15 suture line layer, or it may follow any of the other patterns in the continuum of layers in the lens. These shot patterns can follow the general geometry of the natural suture lines, i.e., a series of star shapes with the number of legs in each star increasing as their placement moves away from the center of the lens. These star shaped shot patterns may follow the precise geometry of the natural suture patterns of the layers of the lens; or it can follow the exact geometry and placement of the sutures, at the same distances as found in the natural lens or as determined by modeling of the natural lens. In all of these utilizations of star patterns one or more stars may be cut. The length of the lines of the legs of the star may be longer, shorter or the same length as the natural suture lines. Moreover, if the length is shorter than the natural length of the suture lines, it may be placed toward the center of the star shape, i.e. the point where the lines join each other, or towards the end of the suture line, i.e., the point furthest on the suture line from the joining point. Further, if the cut is towards the end of the suture line it may extend beyond the suture line or may be co-terminus therewith. Moreover, partial star shaped cuts can be used, such as cuts having a "V" shape, or vertical or horizontal or at an angle in between. These linear cuts, discussed above, are in general referred to herein as laser created suture lines. Moreover, laser created suture lines may be grouped together to in effect form a shell or partial shell.

Figure 3:
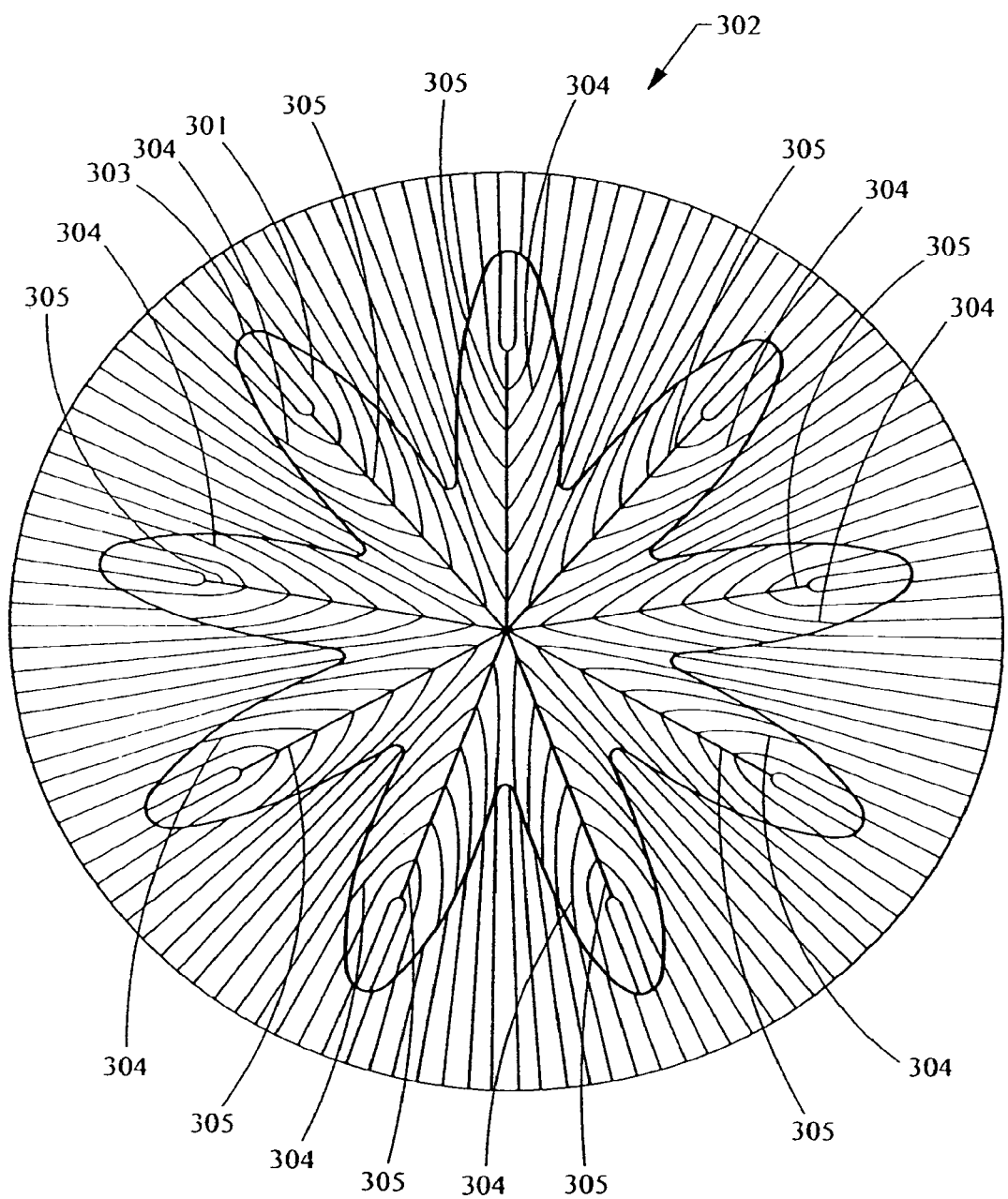
FIG. 3 is a diagram of the anterior surface of a lens normal to the AP axis illustrating a laser shot pattern having a flower like shape which has a contour generally following approximately the last 15% of the fiber length from the end of the fiber.

At present, it is theorized that the use of cuts near the end of the suture lines will have the greatest effect on increasing accommodative amplitude because it is believed that the ends of fibers near the anterior and posterior poles (the point where the AP axis intersects the lens) of the lens are more free to move then the portions of fibers near the equator where there is a greater number of gap junctions which bind fiber faces. At present, it is postulated that it is approximately the last 15% of the fiber length that is most free in the youthful lens with high accommodative amplitude. It is further theorized that fiber layers tend to become bound with age due to a combination of increase in surface roughness and compaction due to growth of fiber layers above. Thus, as illustrated in FIG. 3 a shot pattern 301 is provided to an anterior portion of a layer 302 of the lens. This shot pattern 301 has a contour 303 that follows the contour of approximately the last 15% of fiber length of fibers, represented by lines 304. Thus, the shell cut resembles the shape of a flower. Additionally, the number of petals in the flower shaped shell should correspond to the number of suture lines 305 at that growth layer. Thus, it is theorized that this partial shell cut and/or cuts will have the effect of unbinding the layers and returning the lens to a more youthful increased amplitude of accommodation. Similarly, using partial shells, annular partial shells or planar partial shells in this general area, i.e., the general area at or near the ends of the suture lines, may be employed for the same reasons. This theory is put forward for the purposes of providing further teaching and to advancing the art. This theory, however, is not needed to practice the invention; and the invention and the claims herein are not bound by or restricted by or to this theory.

The use of laser created suture lines, including star shaped patterns may also be used in conjunction with shells, partial shells and planar partial shells. With a particular laser shot pattern, or series of shot patterns, employing elements of each of these shapes. These patterns may be based upon the geometry shown in FIGS. 4-7 as well as the 15 suture line geometry discussed herein; they may follow that geometry exactly, in whole or in part; and/or they may follow that geometry, in whole or in part, as well as following the position of that geometry in the lens. Although a maximum of 15 suture lines is known in the natural lens, more than 15 laser created suture lines may be employed. Moreover, as provided herein, the lens has multiple layers with a continuum of suture lines ranging from 3 to 15 and thus, this invention is not limited to the suture patents of FIGS. 4-7, but instead covers any number of suture lines from 3 to 15, including fractions thereof.

The delivery of shot patterns for the removal of lens material is further provided. A shot pattern that cuts the lens into small cubes, which cubes can then be removed from the lens capsule is provided. The cubes can range in size from a side having a length of about 100 μm to about 4 mm, with about 500 μm to 2 mm being a preferred size. Additionally, this invention is not limited to the formation of cubes and other volumetric shapes of similar general size may be employed. In a further embodiment the laser is also used to create a small opening, capsulorhexis, in the lens anterior surface of the lens capsule for removal of the sectioned cubes. Thus, this procedure may be used to treat cataracts. This procedure may also be used to remove a lens having opacification that has not progressed to the point of being cataractous. This procedure may further be used to remove a natural lens that is clear, but which has lost its ability to accommodate. In all of the above scenarios, it being understood that upon removal of the lens material the lens capsule would subsequently house a suitable replacement, such as an IOL, accommodative IOL, or synthetic lens refilling materials. Moreover, the size and the shape of the capsulorhexis is variable and precisely controlled and preferably is in 2 mm or less diameter for lens refilling applications and about 5 mm for IOLs. A further implementation of the procedure to provide a capsulorhexis is to provide only a partially annular cut and thus leave a portion of the capsule attached to the lens creating a hinged flap like structure. Thus, this procedure may be used to treat cataracts.

It is further provided that volumetric removal of the lens can be performed to correct refractive errors in the eye, such as myopia, hyperopia and astigmatism. Thus, the laser shot pattern is such that a selected volume and/or shape of lens material is removed by photodisruption from the lens. This removal has the affect of alternating the lens shape and thus reducing and/or correcting the refractive error. Volumetric removal of lens tissue can be preformed in conjunction with the various shot patterns provided for increasing accommodative amplitude. In this manner both presbyopia and refractive error can be addressed by the same shot pattern and/or series of shot patterns. The volumetric removal of lens tissue finds further application in enhancing corrective errors for patients that have had prior corneal laser visions correction, such as LASIK, and/or who have corneas that are too thin or weak to have laser corneal surgery.

In all of the laser shot patterns provided herein it is preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed; resulting in a structural change affecting accommodative amplitude and/or refractive error and/or the removal of lens material from the capsule. Shot spacing of lesser or greater distances are contemplated herein and include overlap as necessary to obtain the desired results. Shot spacing considerations include gas bubble dissipation, volume removal efficiency, sequencing efficiency, scanner performance, and cleaving efficiency among others. For example, by way of illustration, for a 5 μm size spot with an energy sufficient to cause photodisruption, a spacing of 20 μm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 μm spot size with a 10 μm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics refers to the effects that take place surrounding photodisruption, such as plasma formation and expansion, shock waive propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 50 MHz to 5 GHz., which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

The terms first, second, third, etc. as used herein are relative terms and must be viewed in the context in which they are used. They do not relate to timing, unless specifically referred to as such. Thus, a first cut may be made after a second cut. In general, it is preferred to fire laser shots in general from posterior points in the laser pattern to anterior points, to avoid and/or minimize the effect of the gas bubbles resulting from prior laser shots. However, because of the varied laser shot patterns that are provided herein, it is not a requirement that a strict posterior to anterior shot sequence be followed. Moreover, in the case of cataracts it may be advantageous to shoot from anterior to posterior, because of the inability of the laser to penetrate substantially beyond the cataract.

Without further elaboration, it is believed that one skilled in the art can, using the preceding description, utilize the present invention to its fullest extent. The following specific embodiments are, therefore, provided as examples of the invention and should be construed as being merely illustrating and not limiting the scope of the invention or the disclosure herein in any way whatsoever.

The following examples are based upon measured lens data and lens data that is obtained by using Burd modeling, which model is set forth in Burd et al., Numerical modeling of the accommodating lens, Visions Research 42 (2002) 2235-2251. The Burd model provides the following algorithm for anterior and/or posterior shape:

$$Z=aR^5+bR^4+cR^3+dR^2+f$$

The coefficients for this algorithm are set forth in Table II.

combinations of horizontal and vertical cuts to cover a specific volume of material. The size of the area that is not cut by these patterns can range from a radius of about 0.1 mm to a radius about 2 mm, specifically from about 0.25 mm to about 1.5 mm, and more specifically as set forth in the following examples. In addition to the cylindrically shaped areas addressed above and in the examples, other shapes for this area may be utilized and would have widths from about 0.5 mm to about 4 mm, specifically from about 0.5 mm to about 3 mm and more specifically about 1 mm, about 2 mm and about 3 mm. Further, this radius or width can vary for different shells in the first cut and for different locations of the second cuts. The use of the terms "first" and "second" in describing this combination of cuts is meant solely for the purpose of identification of these cuts. These terms are not intended to and do not imply that one cut is made before or after the other. In fact, all sequences of making these cuts are contemplated. Additionally, it being readily understood that the shell cut is formed by and thus corresponds to a laser shot pattern. Specific examples of such combinations of shot patterns are provided by way of illustration in the following Examples 1-6, and are not meant to limit the scope of such combinations.

Figure 13:
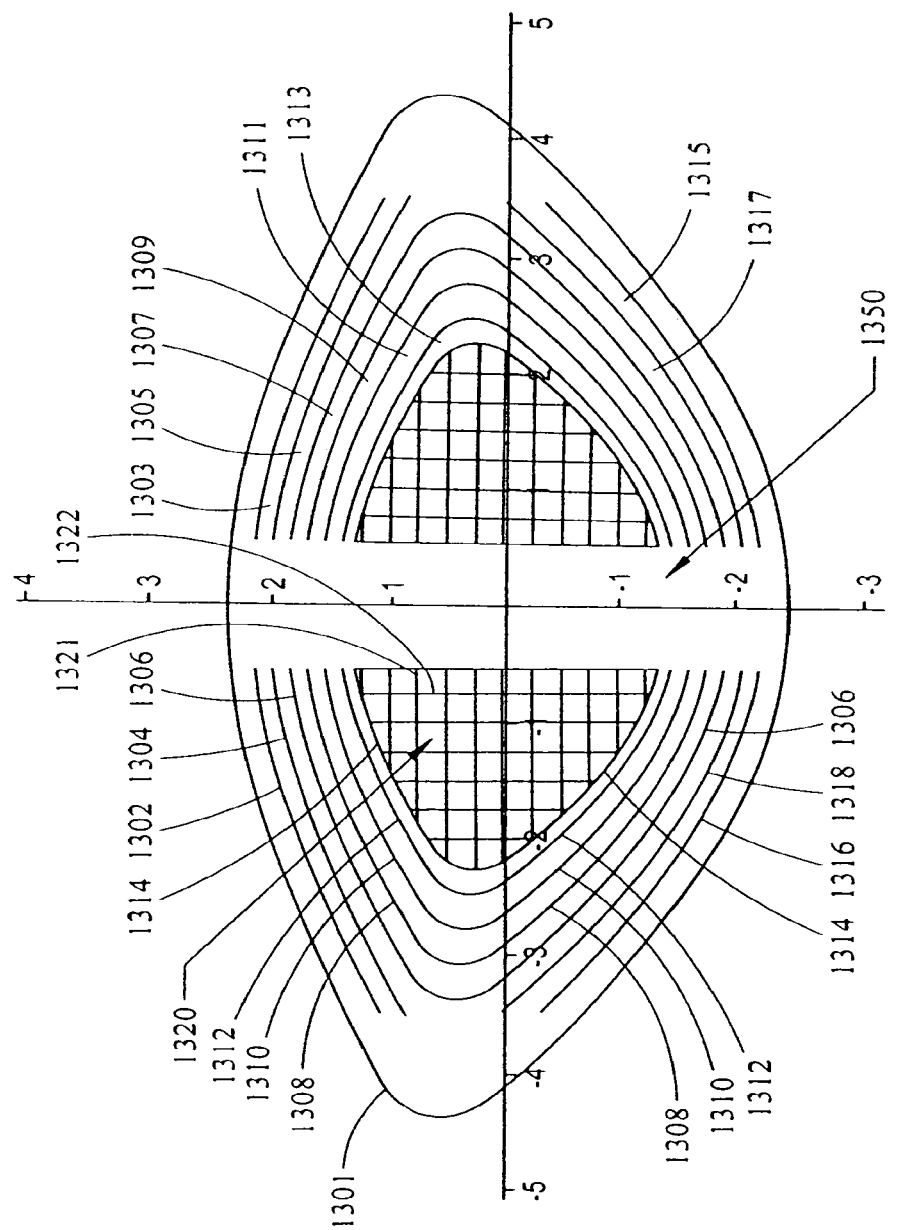
FIGS. 13-21 are cross-section drawings of lens illustrating a laser shot pattern.

EXAMPLE 1 provides for making of nested, lens shaped shell cuts in combination with cube shaped cuts. The laser shot patterns for this example are illustrated in FIG. 13. In this Figure there is shown the outer surface 1301 of a lens. There is further provided a series of nested or essentially concentric shells and shell cuts, which essentially follow the shape of the lens. Thus, there is provided annular shell cuts 1302, 1304, 1306, 1308, 1310, 1312, 1314, 1316, and 1318. Shell cuts 1302 and 1304 are positioned nearer to and follow the anterior surface of the lens, while shell cuts 1316 and 1318 are positioned nearer to and follow the posterior

TABLE II

|  | a | b | c | d | f |
|---|---|---|---|---|---|
| Anterior (11-year) | −0.00048433393427 | 0.00528772036011 | −0.01383693844808 | −0.07352941176471 | 2.18 |
| Posterior (11-year) | 0.00300182571400 | −0.02576464843559 | 0.06916082660799 | 0.08928571428571 | −2.13 |
| Anterior (29-year) | −0.00153004454939 | 0.01191111565048 | −0.02032562095557 | −0.07692307692308 | 2.04 |
| Posterior (29-year) | 0.00375558685672 | −0.03036516318799 | 0.06955483582257 | 0.09433962264151 | −2.09 |
| Anterior (45-year) | −0.00026524088453 | 0.00449862869630 | −0.01657250977510 | −0.06578947368421 | 2.42 |
| Posterior (45-year) | 0.00266482873720 | −0.02666997217562 | 0.08467905191557 | 0.06172839506173 | −2.42 |

Figure 9:
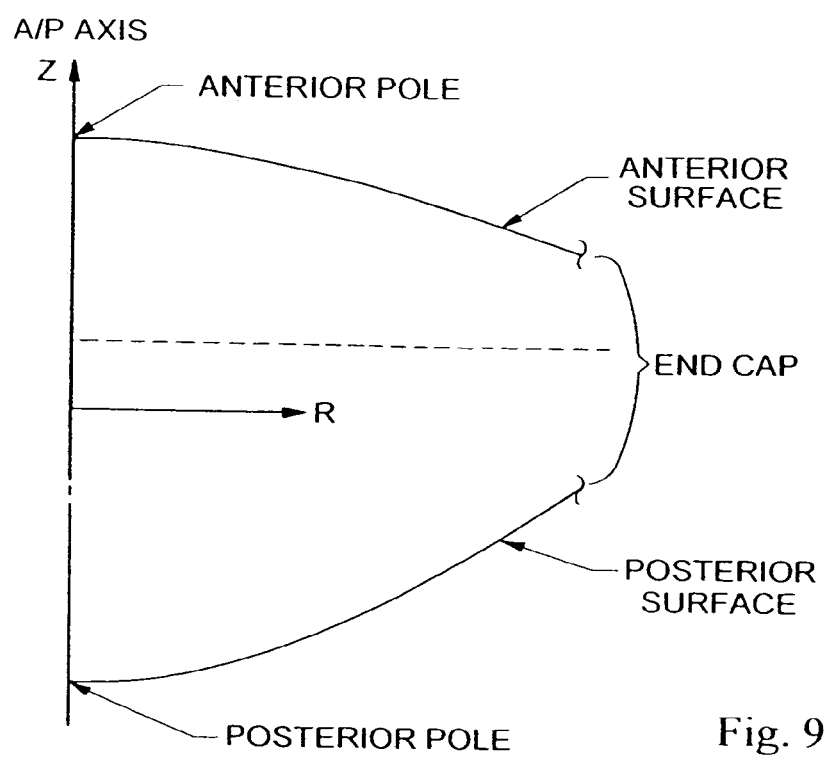
FIG. 9 is a cross-section drawing of the lens relating to the model developed by Burd.

Additionally, the variables Z and R are defined by the drawing FIG. 9.

Figure 10:
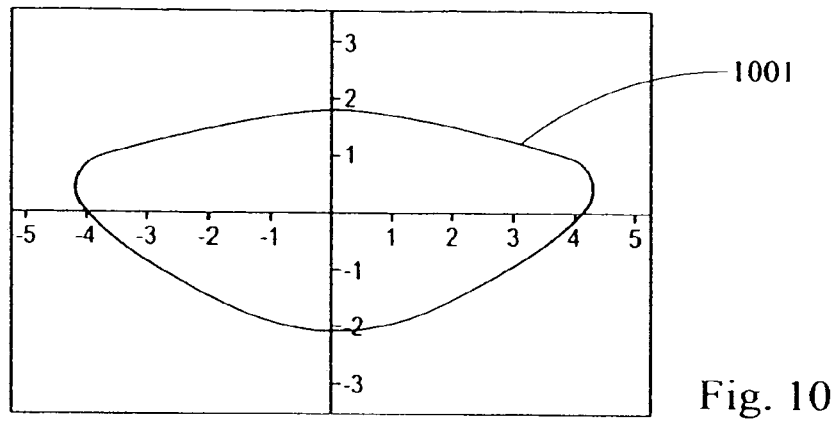
FIG. 10 is a cross-section drawing of a lens based upon the model developed by Burd.
Figure 11:
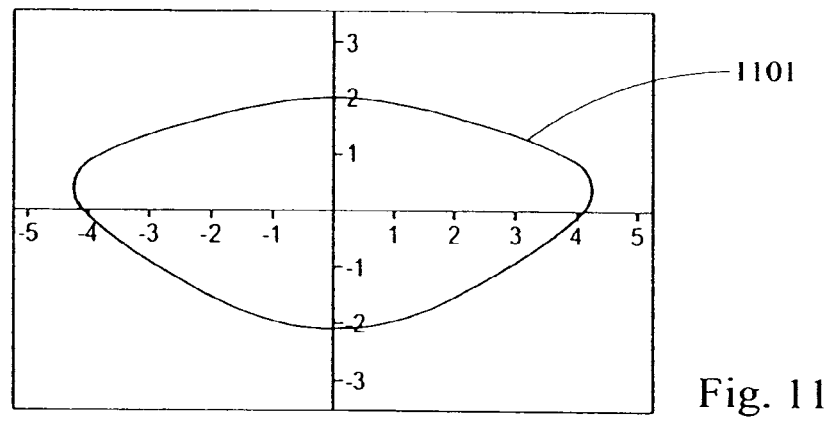
FIG. 11 is a cross-section drawing of a lens based upon the model developed by Burd.
Figure 12:
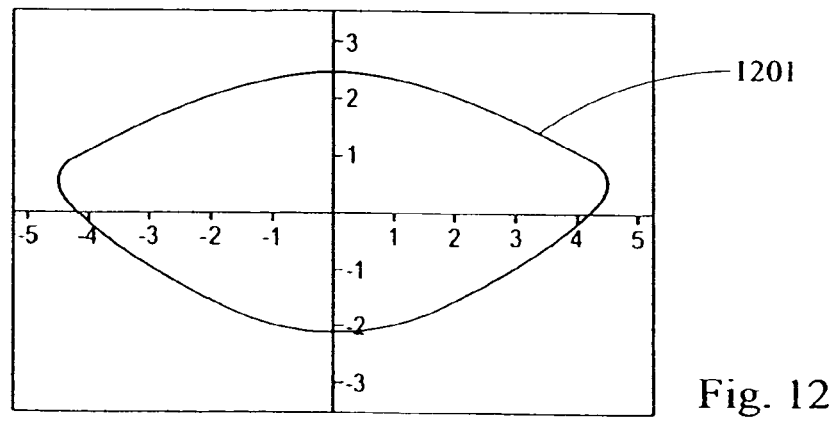
FIG. 12 is a cross-section drawing of a lens based upon the model developed by Burd.
Figure 23:
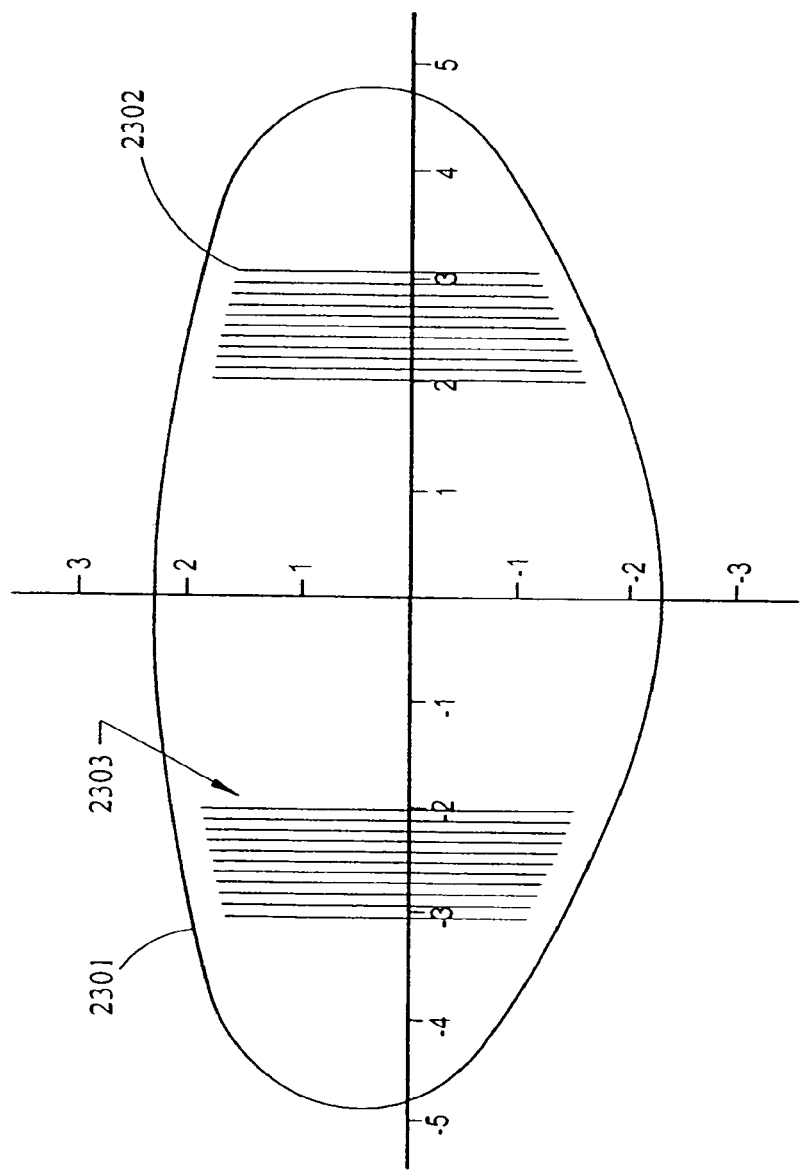
FIGS. 23-24 are cross-section drawings of lens illustrating vertical laser shot patterns.
Figure 24:
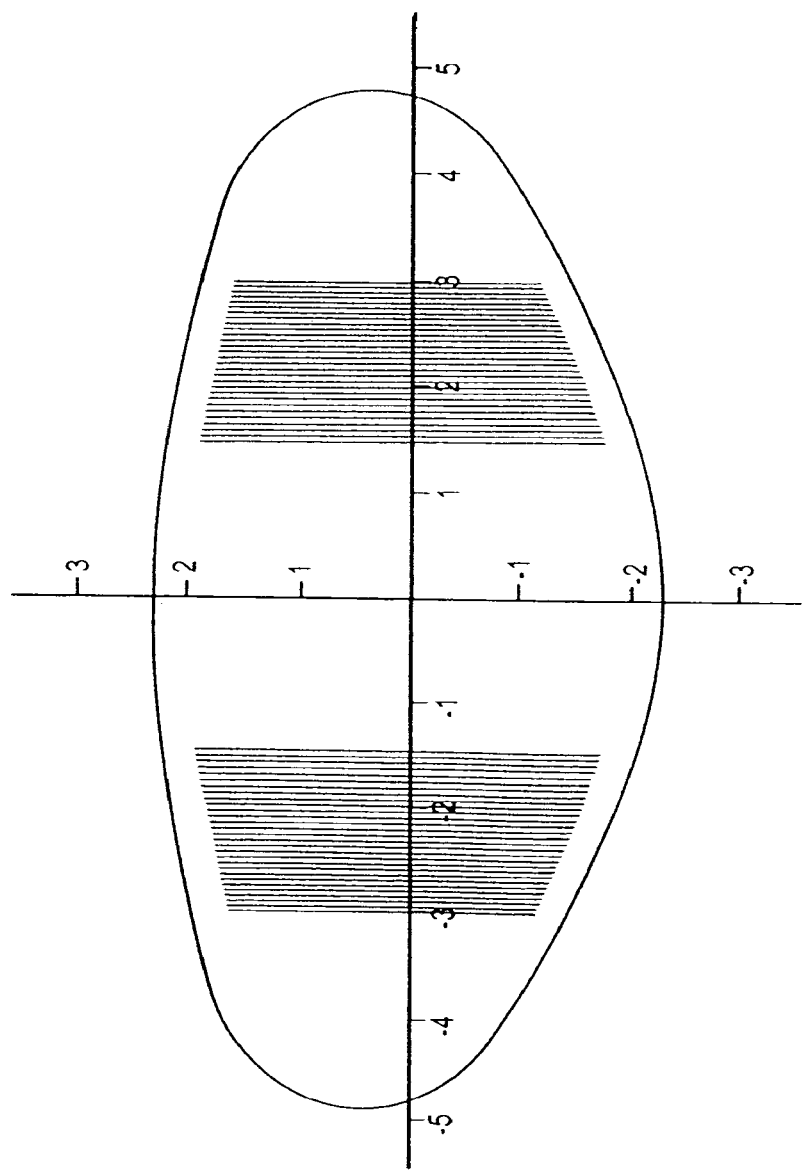

Thus, FIGS. 10, 11 and 12 provide cross sectional views of the lens having an outer surface 1001, 1101, 1201 for three ages, 18, 29 and 45-year old respectively, based upon the Burd model and show growth in size along with shape changes with age. The units for the axes on these drawings, as well as for FIGS. 13, 23 and 24 are in millimeters (mm).

A combination of first cuts to create nested shells that in general follow the shape of and are positioned near the outer surface of the lens and second cuts to create a pattern directed toward the inner portions of the lens, with both the first cuts and the second cuts not cutting the material near the optical axis of the lens is provided. This combination of cuts, with a central portion of the lens avoided, provides for both an increase in accommodative amplitude, as well as, an increase in the refractive power of the lens. The first cuts can range from one shell to many nested shells. They can be in the form of partial or complete shells, or a combination of both. In the case of partial shells they can be annular. The second cuts can be shells, cubes, or other patterns including surface of the lens. Shell cuts 1306, 1308, 1310, 1312 and 1314 follow the entire curvature of the lens from anterior to posterior. The shell cuts form shells 1303, 1305, 1307, 1309, 1311, 1313, 1315, and 1317. These shells and shell cuts form annular structures but are illustrated in FIG. 13 in cross-section. As such, the shells or cuts on the left side of the figure correspond to, and are part of, the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 1320 of horizontal 1321 and vertical 1322 cuts. Shell cut 1314 borders and is joined with cube cuts 1321 and 1322. Such a shell cut may be, but is not required to be present. Further, as provided in FIG. 13, both these second cuts (cube cuts 1320) and the first cuts (shell cuts 1302, 1304, 1306, 1308, 1310, 1312, 1314, 1316, and 1318) are removed away from the optical axis of the lens by about 0.5 mm and thus form a cylinder of uncut lens material 1350 that has a radius of about 0.5 mm (diameter of about 1 mm). Thus, there is shown in this figure a plurality of cuts and cube pattern that provide a series of annular cuts surrounding a central portion of the lens that is not altered by the laser.

Figure 14:
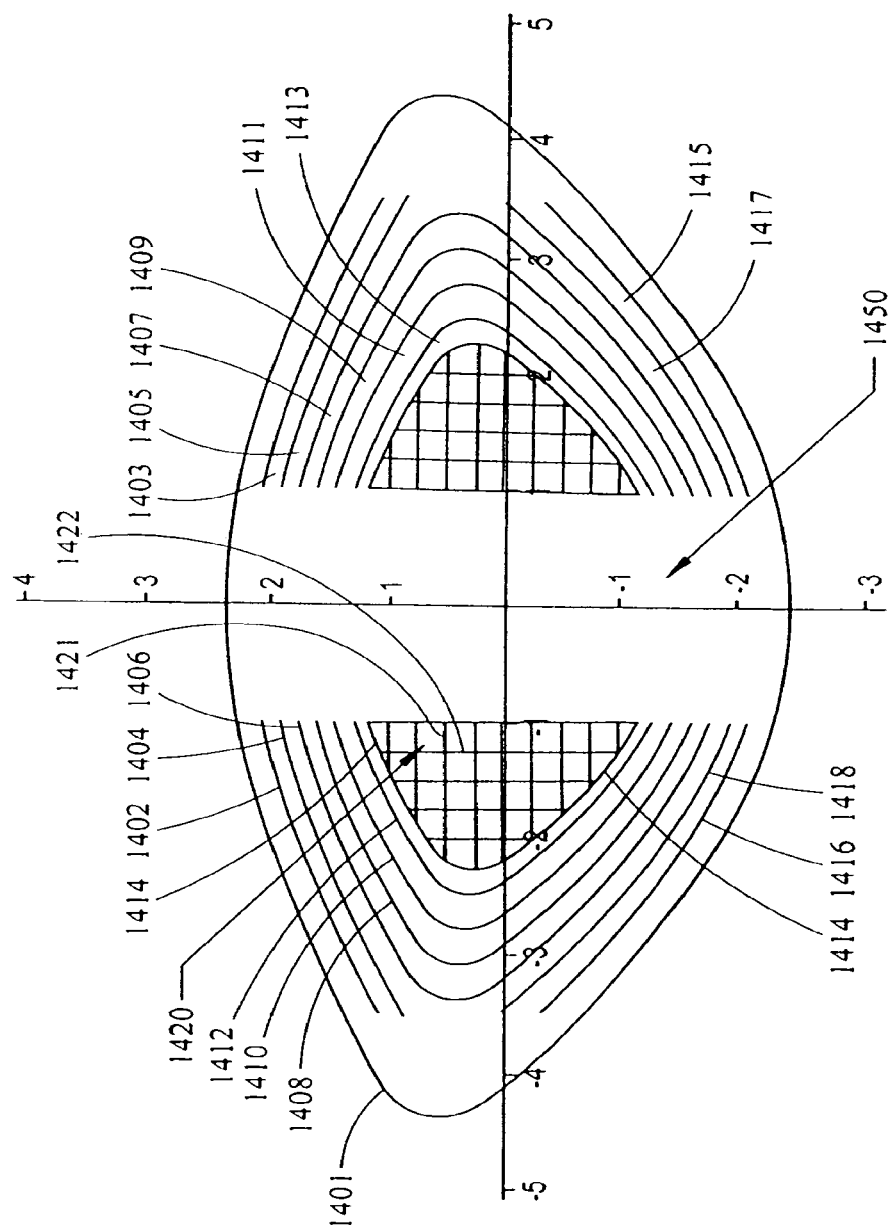

EXAMPLE 2 provides for making of nested, lens shaped shell cuts in combination with cube shaped cuts. The laser shot patterns for this example are illustrated in FIG. 14. In this Figure there is shown the outer surface 1401 of a lens. There is further provided a series of nested or essentially concentric shells and shell cuts, which essentially follow the shape of the lens. Thus, there is provided annular shell cuts 1402, 1404, 1406, 1408, 1410, 1412, 1414, 1416, and 1418. Shell cuts 1402 and 1404 are positioned nearer to and follow the anterior surface of the lens, while shell cuts 1416 and 1418 are positioned nearer to and follow the posterior surface of the lens. Shell cuts 1406, 1408, 1410, 1412 and 1414 follow the entire curvature of the lens from anterior to posterior. The shell cuts form shells 1403, 1405, 1407, 1409, 1411, 1413, 1415, and 1417. These shells and shell cuts form annular structures but are illustrated in FIG. 14 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 1420 of horizontal 1421 and vertical 1422 cuts. Shell cut 1414 borders and is joined with cube cuts 1421 and 1422. Such a shell cut may be, but is not required to be present. Further, as provided in FIG. 14, both these second cuts (cube cuts 1420) and the first cuts (shell cuts 1402, 1404, 1406, 1408, 1410, 1412, 1414, 1416, and 1418) are removed away from the optical axis of the lens by about 1 mm and thus form a cylinder of uncut lens material 1450 that has a radius of about 1 mm (diameter of about 2 mm). Thus, there is shown in this figure a plurality of cuts and cube pattern that provide a series of annular cuts surrounding a central portion of the lens that is not altered by the laser.

Figure 15:
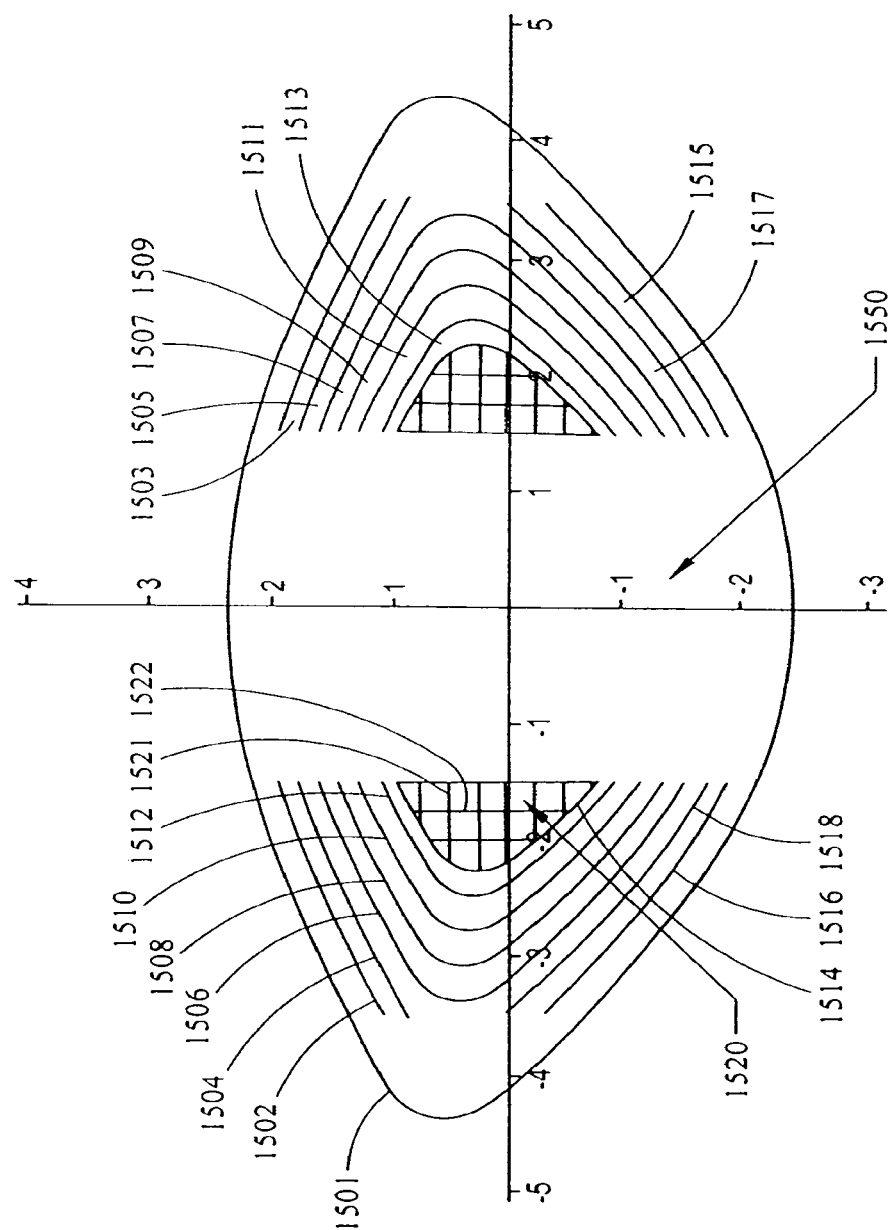

EXAMPLE 3 provides for making of nested, lens shaped shell cuts in combination with cube shaped cuts. The laser shot patterns for this example are illustrated in FIG. 15. In this Figure there is shown the outer surface 1501 of a lens. There is further provided a series of nested or essentially concentric shells and shell cuts, which essentially follow the shape of the lens. Thus, there is provided annular shell cuts 1502, 1504, 1506, 1508, 1510, 1512, 1514, 1516, and 1518. Shell cuts 1502 and 1504 are positioned nearer to and follow the anterior surface of the lens, while shell cuts 1516 and 1518 are positioned nearer to and follow the posterior surface of the lens. Shell cuts 1506, 1508, 1510, 1512 and 1514 follow the entire curvature of the lens from anterior to posterior. The shell cuts form shells 1503, 1505, 1507, 1509, 1511, 1513, 1515, and 1517. These shells and shell cuts form annular structures but are illustrated in FIG. 15 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a cube pattern 1520 of horizontal 1521 and vertical 1522 cuts. Shell cut 1514 borders and is joined with cube cuts 1521 and 1522. Such a shell cut may be, but is not required to be present. Further, as provided in FIG. 15, both these second cuts (cube cuts 1520) and the first cuts (shell cuts 1502, 1504, 1506, 1508, 1510, 1512, 1514, 1516, and 1518) are removed away from the optical axis of the lens by about 1.5 mm and thus form a cylinder of uncut lens material 1550 that has a radius of about 1.5 mm (diameter of about 3 mm). Thus, there is shown in this figure a plurality of cuts and cube pattern that provide a series of annular cuts surrounding a central portion of the lens that is not altered by the laser.

Figure 16:
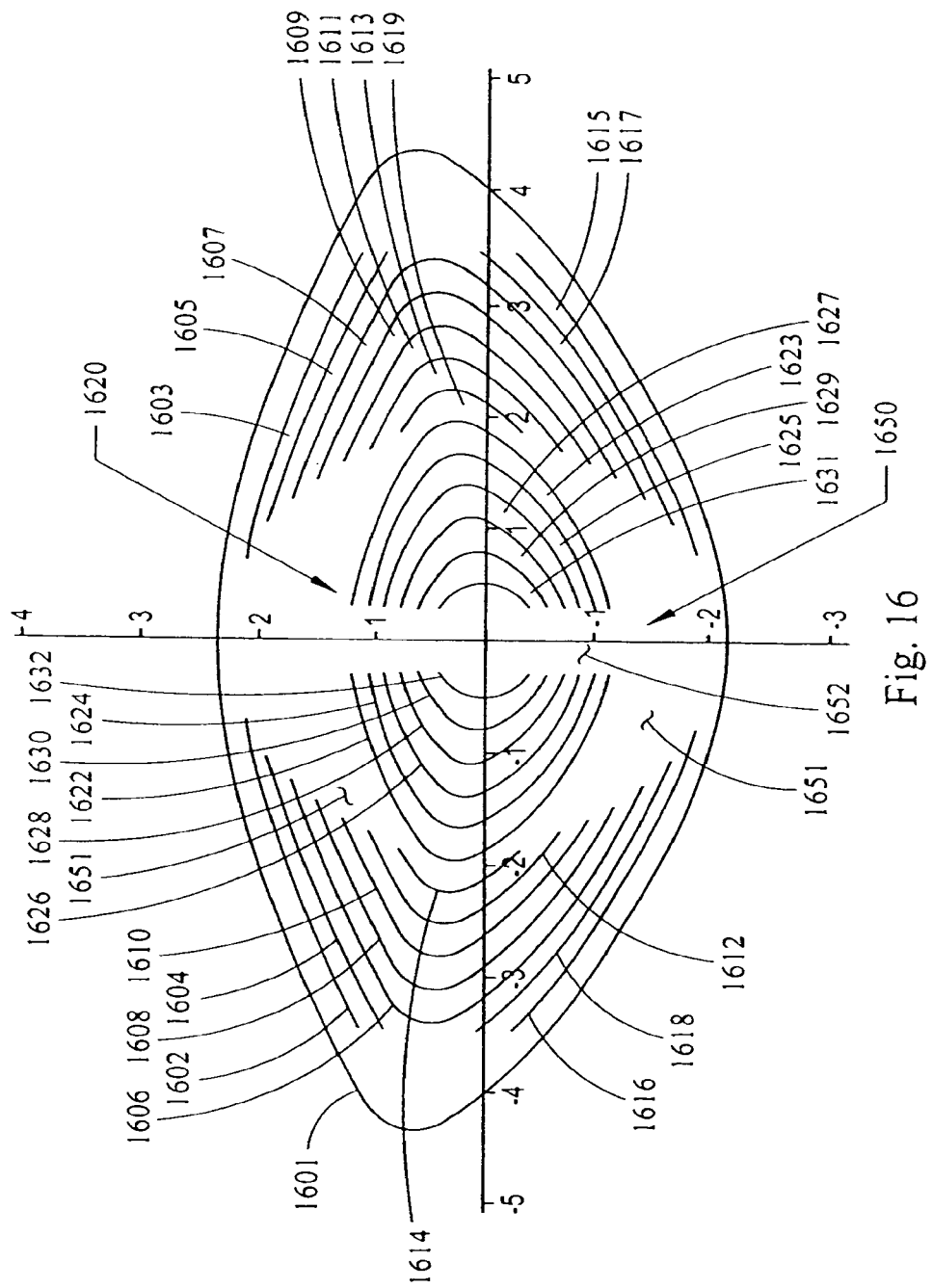

EXAMPLE 4 provides for making of nested, lens shaped shell cuts in combination with cube shaped cuts. The laser shot patterns for this example are illustrated in FIG. 16 In this Figure there is shown the outer surface 1601 of a lens. There is further provided a series of nested or essentially concentric shells and shell cuts, which essentially follow the shape of the lens. Thus, there is provided annular shell cuts 1602, 1604, 1606, 1608, 1610, 1612, 1614, 1616, and 1618. Shell cuts 1602 and 1604 are positioned nearer to and follow the anterior surface of the lens, while shell cuts 1616 and 1618 are positioned nearer to and follow the posterior surface of the lens. Shell cuts 1606, 1608, 1610, 1612 and 1614 follow the entire curvature of the lens from anterior to posterior. The shell cuts form shells 1603, 1605, 1607, 1609, 1611, 1613, 1615, 1617 and 1619. These shells and shell cuts form annular structures but are illustrated in FIG. 16 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a shell pattern 1620 of nested or essentially concentric shell cuts 1622, 1624, 1626, 1628, 1630 and 1632 which form shells 1623, 1625, 1627, 1629 and 1631. Further, as provided in FIG. 16, both these second cuts 1620 and the first cuts (shell cuts 1602, 1604, 1606, 1608, 1610, 1612, 1614, 1616, and 1618) are removed away from the optical axis of the lens. In this example, by varying the distance from about 0.25 mm for cuts 1620 and from about 0.75 mm to about 2 mm for cuts 1602 et. seq., there is provided a way to form a cylindrical like area of uncut lens material 1650. This area of uncut lens material has a portion of essentially uniform radius 1652 (note that inner cut 1632 is arcuate) of about 0.25 mm (diameter of about 0.5 mm) and a portion having a changing radius 1651, varying from a radius of about 0.75 mm (diameter of about 1.5 mm) for cut 1616 to about 2 mm (diameter of about 4 mm) for cut 1614. In the area of changing radius 1651 it can be seen that the change in radius/cut in this example is non-linear, with cut 1602 having a radius of about 0.75 mm, cut 1604 having a radius of about 1 mm, cut 1606 having a radius of about 1.25 mm, cut 1608 having a radius of about 1.4 mm, cut 1610 having a radius of about 1.6 mm, cut 1612 having a radius of about 1.7 mm, and cut 1614 having a radius of about 1.8 mm. Thus, there is shown in this figure a plurality of cuts that provide a series of annular cuts surrounding a central portion of the lens that is not altered by the laser.

Figure 17:
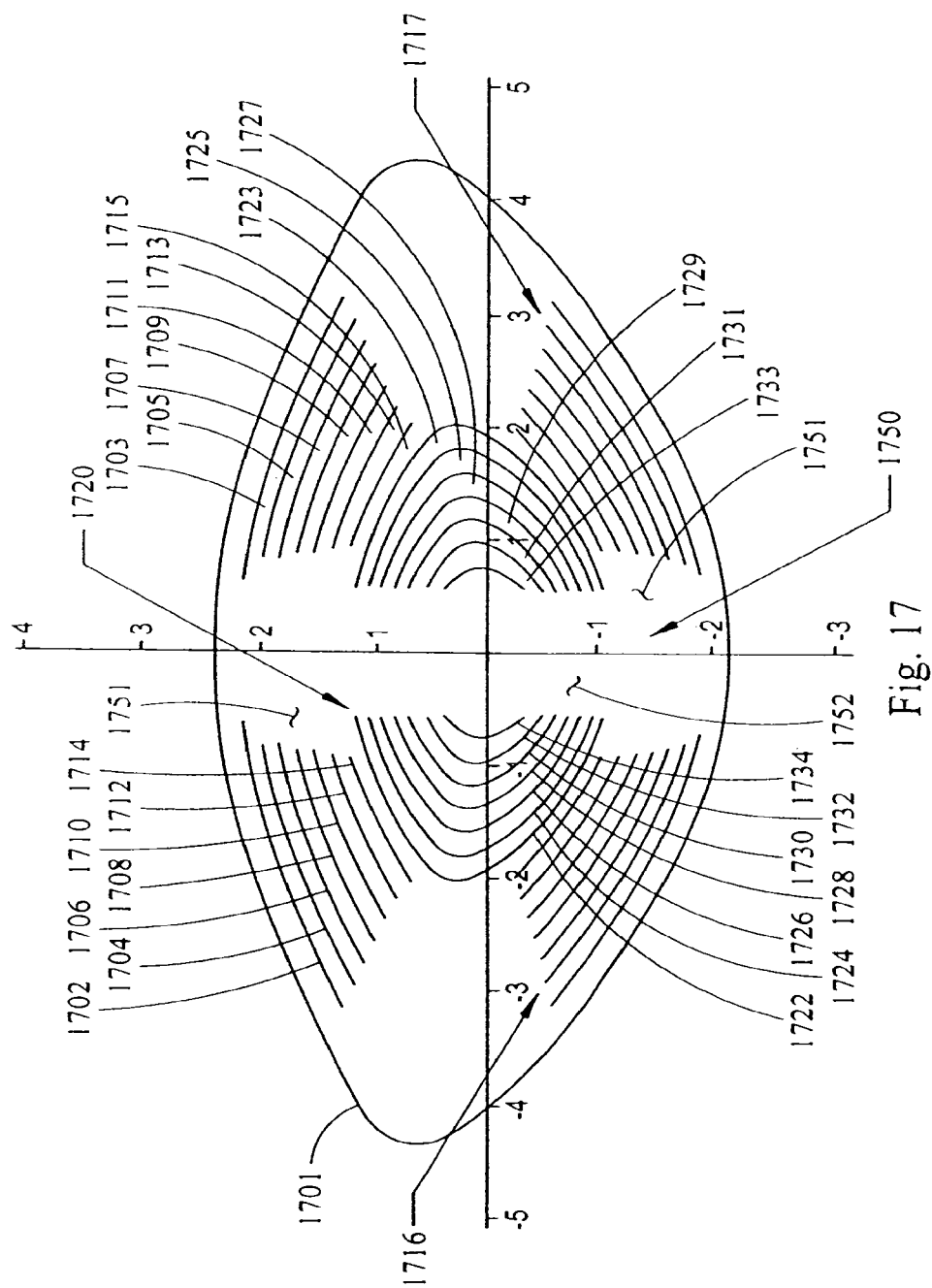

EXAMPLE 5, provides for making of nested, lens shaped shell cuts in combination with cube shaped cuts. The laser shot patterns for this example are illustrated in FIG. 17. In this Figure there is shown the outer surface 1701 of a lens. There is further provided a series of nested or essentially concentric shells and shell cuts, which essentially follow the shape of the lens. Thus, there is provided annular shell cuts

1702, 1704, 1706, 1708, 1710, 1712, and 1714, which follow the anterior shape of the lens. There is further provided a series of nested or essentially concentric shell cuts, collectively, 1716, which follow the posterior surface of the lens, and but for the difference in shape of the posterior and anterior surface of the lens, are essentially mirror images of cuts 1702 et. seq. None of the shell cuts 1702 et. seq. or 1716 follow the entire curvature of the lens from anterior to posterior. The shell cuts form shells 1703, 1705, 1707, 1709, 1711, 1713, 1715, and 1717 and, collectively, 1717. These shells and shell cuts form annular structures but are illustrated in FIG. 17 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a shell pattern 1720 of nested or essentially concentric shell cuts 1722, 1724, 1726, 1728, 1730, 1732 and 1734, which form shells 1723, 1725, 1727, 1729, 1731 and 1733. Further, as provided in FIG. 17, both these second cuts 1720 and the first cuts (shell cuts 1702, 1704, 1706, 1708, 1710, 1712, 1714 and 1716) are removed away from the optical axis of the lens. There is provided a cylindrical like area of uncut lens material 1750. This area of uncut lens material has a portion of essentially uniform radius 1752 (note that inner cut 1734 is arcuate) of about 0.25 mm (diameter of about 0.5 mm) and a portion having a changing radius 1751. Thus, there is shown in this figure a plurality of cuts that provide a series of annular cuts surrounding a central portion of the lens that is not altered by the laser.

Figure 18:
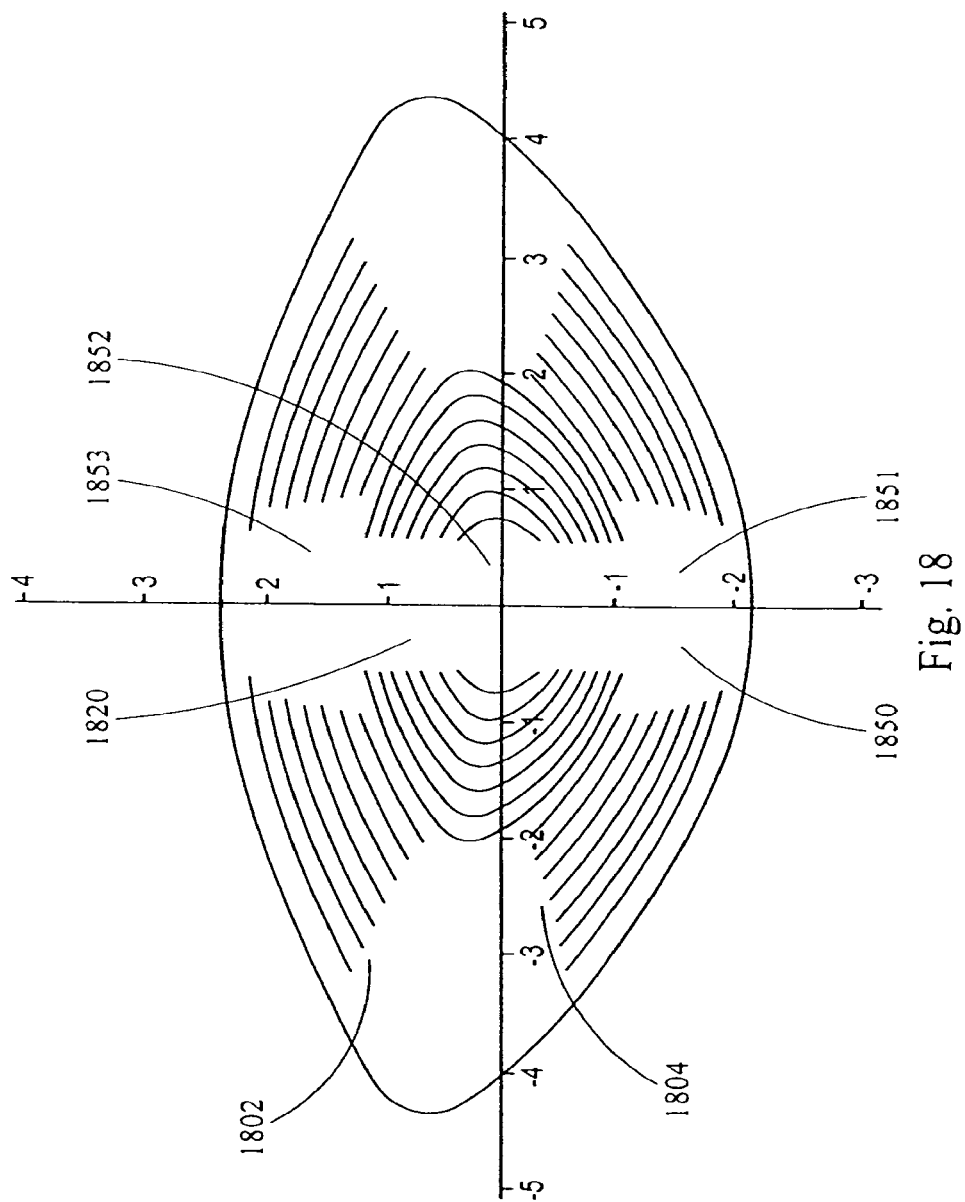

EXAMPLE 6 provides for making of nested, lens shaped shell cuts in combination with cube shaped cuts. The laser shot patterns for this example are illustrated in FIG. 18 In this Figure there is shown the outer surface 1801 of a lens. There is further provided a first series of nested or essentially concentric shells and shell cuts, which essentially follow the shape of the lens. Thus, there is provided annular shell cuts collectively 1802 and 1804. Cuts 1802 follow the anterior shape of the lens. Cuts 1804 follow the posterior surface of the lens. None of these shell cuts 1802, 1804, follow the entire curvature of the lens from anterior to posterior. These shell cuts form shells (shown but not numbered). These shells and shell cuts form annular structures but are illustrated in FIG. 18 in cross-section. As such, the shells or cuts on the left side of the figure correspond to, and are part of the shells or cuts shown on the right side of the figure. These shells or partial shells are designed to increase flexibility in the lens by decreasing the strength of nested fiber layers by separating the bound layers, which it is theorized would reduce the structural strength and increase deflection for a given load or force.

There is further provided a second series of cuts in a pattern of nested or essentially concentric shell cuts, collectively 1820, which form shells (shown but not numbered). Further, as provided in FIG. 18, both these second cuts 1820 and the first cuts 1802, 1804 are removed away from the optical axis of the lens. There is provided a cylindrical like area of uncut lens material 1750. This area of uncut lens material has a portion of essentially uniform radius 1752 (note that the inner most cut is arcuate) and portions having varying or changing radii 1851, 1853. In this example, the change in radius is different between the posterior 1851 and anterior 1853 sides. Further, the outer radii for these cuts 18002, 1804, varies and in this example is different for the anterior and posterior side cuts. Thus, there is shown in this figure a plurality of cuts that provide a series of annular cuts surrounding a central portion of the lens that is not altered by the laser.

Various combinations of first and second shell cuts can be employed. Thus, the first and second patterns of any of Examples 1 through 6 may be used with any of the other first and second patterns of those examples. Similarly, any of these patterns may also be used in conjunction with the other patterns and teachings of patterns provided in this specification, including the patterns that are incorporated herein by reference. Moreover, when utilizing the teachings of these examples regarding varying or changing radii for uncut areas, the change in those radii per cut can be uniform, non-uniform, linear or non-linear. Moreover, such changes in radii per cut for either or both the interior radii (closest to the optical axis of the eye) or the outer radii can be the same from the anterior to the posterior side or the changes can be different from the anterior to posterior side cuts.

Although not bound by this theory, it theorized that increasing the deflection of the lens for a given load or zonule force will increase the flexibility of the lens structure and, in turn, the amplitude of accommodation for that same zonule force. Further, it is theorized that by providing these annular shells in conjunction with the cylindrical cuts and unaffected center portion of the lens, for example 1350, 1450, 1550, 1650, 1750, and 1850, that the shape of the lens will be altered in a manner that provides for an increase in the refractive power of the lens. Thus, the combination of these first and second cuts provides for both improved accommodative amplitude and increased refractive power of the lens.

A further application of laser shot patterns is to create an area of opacification in the lens, which opacification functions to provide a limiting aperture in the lens, which limiting aperture is smaller than the dark adapted pupil diameter. Use of a limiting aperture in the visual system improves depth of field, depth of focus and image quality. Thus, It is believed that creating such a limiting aperture within the lens will provide these benefits and may for example assist in the ability to see and read printed materials. Moreover, it is believed that the creation of such a limiting aperture can be combined with the creation of other cuts and structures within the lens, which cuts and structures are for the purpose of increasing refractive power and improving accommodative amplitude, as taught for example in this specification and the pending specifications that are incorporated herein by reference. Thus, it is believe that this combination of limiting apertures and other structures will have an additive effect to improving vision and especially near vision.

Such a limiting aperture would be provided by the creation of an annulus of opacified lens material. The inner diameter for this annulus of opacified material would be between about 1 to about 4 mm and the outside diameter would be between about 4 to about 7 mm. The degree of opacification in the annulus is not necessarily 100% blocking, but must be blocking enough to reduce negative visual symptoms. Thus, for example, about 90%, about 80%, from about 20% to about 100%, and more specifically from about 50% to about 100% opacification within the annulus, as measures by the amount of light blocked, i.e. 100% minus the transmission percentage, are provided. This opacified annulus is positioned essentially central to the optical axis of the lens or essentially central to the natural pupil. Additionally, the limiting aperture may be located at any point between the anterior and posterior surfaces of the lens. To create such an opacified annulus in the lens the laser parameters would be chosen to have sufficient excess energy or energy density, when compared with that which is required for meeting minimum photo disruption threshold, to cause the lens material to retain a degree of opacification. Moreover, by way of example, other sources of excess energy, including thermal energy, for the creation of the opacified lens aperture may be obtained by choosing lasers with longer pulse widths, including but not limited to, those that extend to continuous wave operation.

Figure 19:
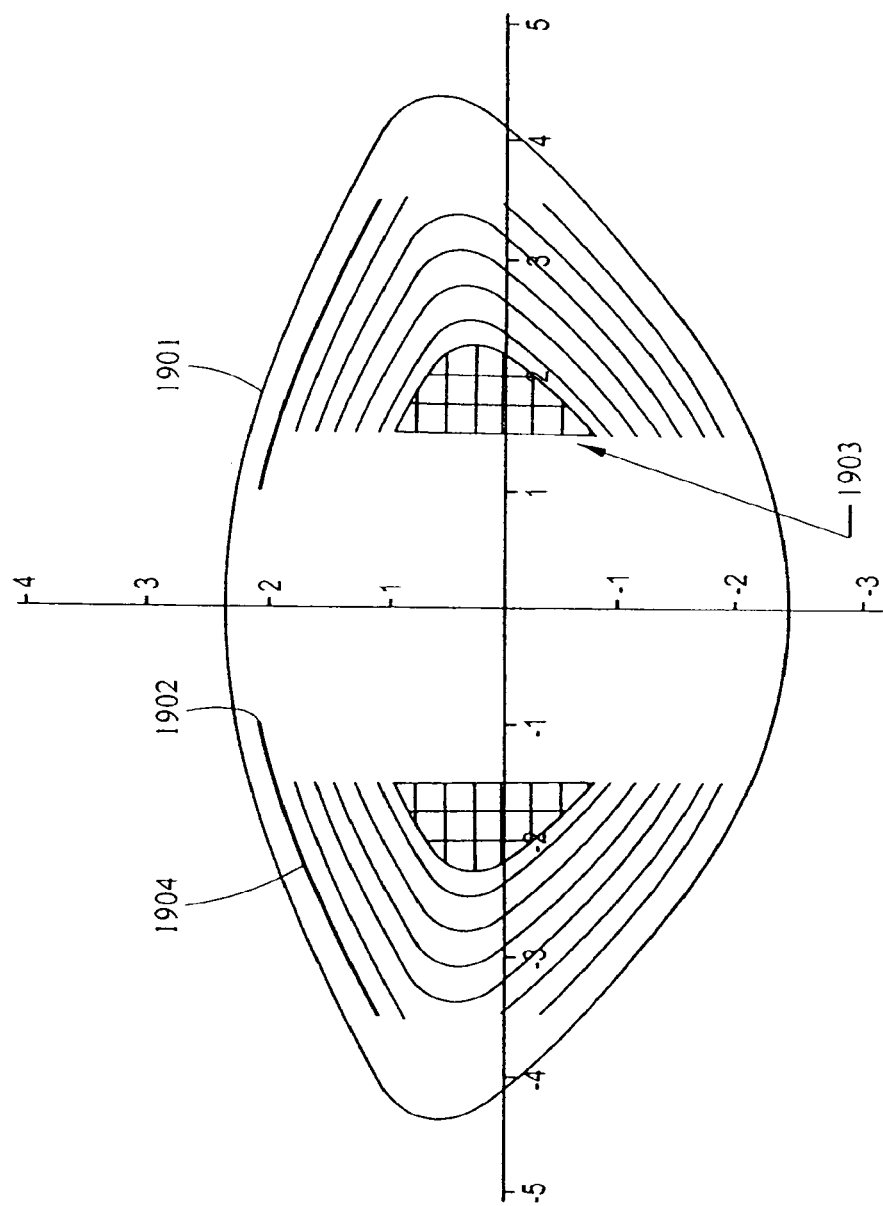

Examples 7 to 9 provide for combinations of limiting apertures, shells and other structures for the proposes of improving accommodative amplitude and increased refractive power. Thus, Example 7, which is illustrated in FIG. 19, provides for a limiting aperture 1902, having a diameter of about 2 mm (radius of about 1 mm), that is located near to the anterior lens surface 1901, as well as, other structures 1903. The limiting aperture 1902 is provided by an opacified annulus 1904, having an outer diameter of about 7 mm.

Figure 20:
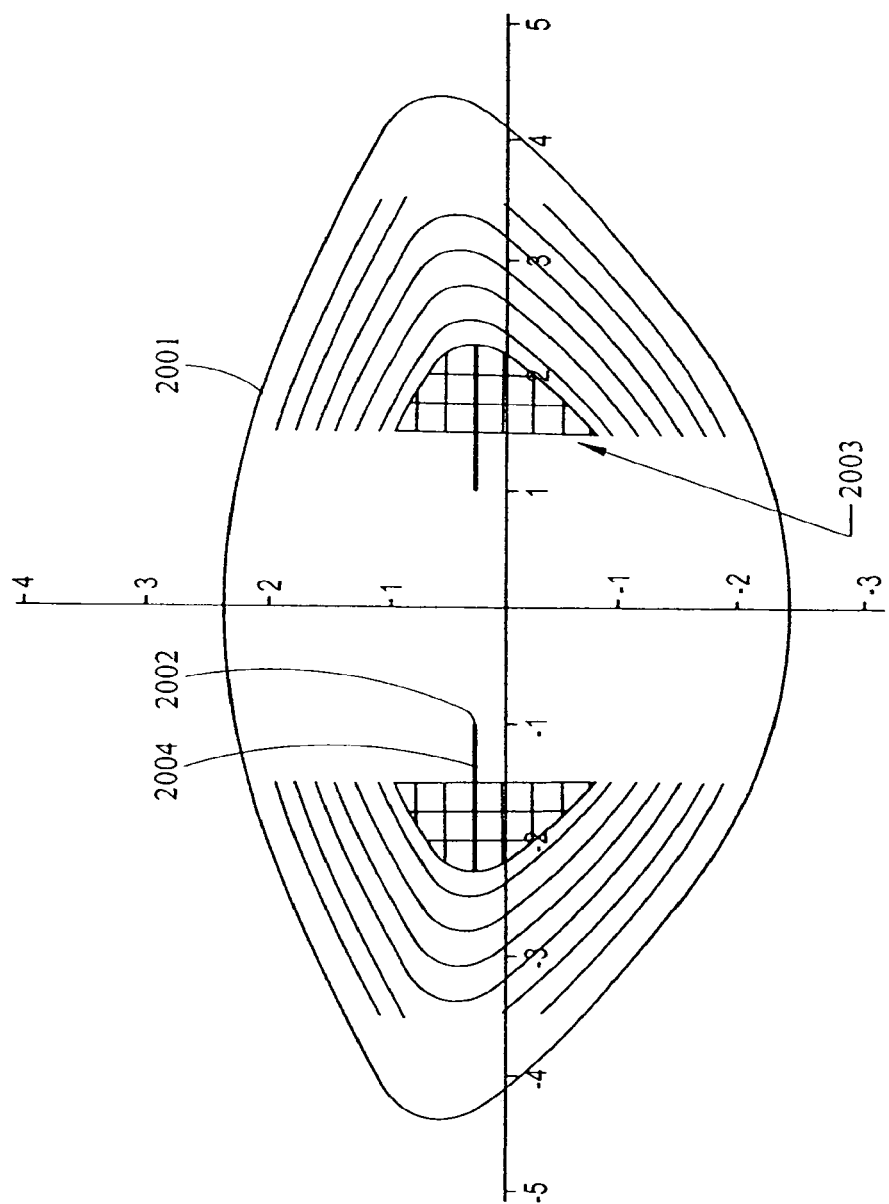

Example 8, which is illustrated in FIG. 20, provides for a limiting aperture 2002, having a diameter of about 2 mm that is located central to the lens surface 2001 (i.e., between the anterior and posterior surfaces of the lens), as well as, other structures 2003. The limiting aperture 2002 is provided by an opacified annulus 2004, having an outer diameter of about 4.5 mm.

Figure 21:
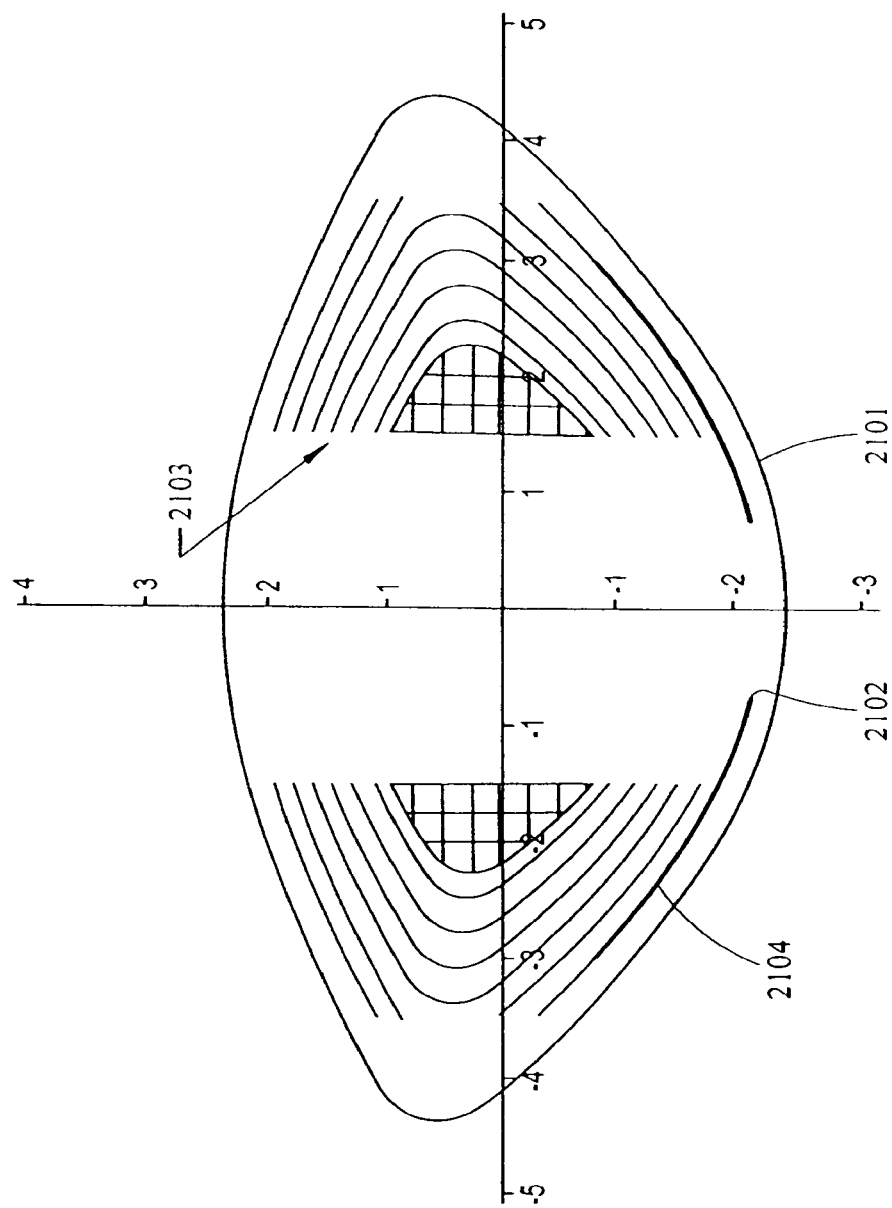

Example 9, which is illustrated in FIG. 21, provides for a limiting aperture 2102, having a diameter of 1.5 mm, that is located near the posterior of the lens surface 2101, as well as other structures 2103. The limiting aperture 2102 is provided by an opacified annulus 2104, having an outer diameter of about 6 mm.

It should further be understood that although the limiting apertures are shown in combination with other structures they can also be used without the presence of those structures. Moreover, although the limiting apertures in these examples are shown as having a smaller inner diameter than the other structures, it should be understood that the inner diameter of some or all of the other structures could be smaller than the inner diameter of the limiting aperture, as these other structures are not opacified. Further, the opacification of the annulus may decrease over time. Thus, retreatment of the lens many be periodically required to maintain the benefits set forth above.

There is further provided the use of substantially vertical shot patterns, that is shot patterns that have cuts that are essentially parallel to the Optical axis of the eye. Thus, Example 10, which is illustrated in FIG. 23, provides an outer surface 2301 of a lens that has a shot pattern that has vertical cuts, e.g., 2302, arranged in a pattern that provides for an annular area of cutting 2303. These figures are show in cross-section and thus the pattern on the right side corresponds to the pattern on the left side. Moreover, as such the density of vertical cut is the same on the left and right side of the figures.

Example 11, which is illustrated in FIG. 24 provides a further example of the use of vertical cuts. In this example there is provided an outer surface 2401 of the lens that has a shot pattern that has vertical cuts, e.g., 2402, arranged in a pattern that provides for an annular area of cutting 2403. These figures are show in cross-section and thus the pattern on the right side corresponds to the pattern on the left side. Moreover, as such the density of vertical cut is the same on the left and right side of the figures. As illustrated, the density of the vertical cuts in Example 11 is substantially greater than the density of shots in Example 10.

The vertical cuts can be separately spaced from each other in the annular area, thus creating a series of parallel disconnected vertical cuts, they can be positioned close enough together to create a series of concentric vertical cylinders.

The inner diameter of the annular area of cutting when using such vertical cuts as illustrated in Examples 10 and 11 is from about 0.5 mm to about 2.5 mm and the outer diameter of such vertical cuts is from about 2 or 3 mm to about 7 or 8 mm.

The use of vertical shot patterns or primarily vertical shot patterns has added advantages in slower laser systems. In particular, the use of vertical shot patterns has added advantages in laser systems slower than F/# equals 1.5 (F/1.5), and in particular slower that F/2. Additionally, the ability to move the shots closer together, i.e., more dense, is obtainable with such vertical shot patterns. Thus, the spacing can be smaller than three times the spot size. Accordingly, fully cleaved horizontal lens sections have been made by using shot densities small that were smaller than three times the spot size, e.g., about 10-20 µm separation for a 10 µm spot.

A coherent optical effect occurs when coherent superposition of optical waves with constructive and destructive interference takes place. Rainbow glare is an example of a coherent optical effect. Such effects can arise when highly regular and spatially periodic optical features are present within an optical system. Thus, to prevent these effects from occurring in the eye as a result of the various cutting of lens tissue described in this specification and the applications that are incorporated herein by reference, it is provided that random or irregular shot spacings be incorporated partially or completely throughout the shot patterns. Thus, for example and by way of illustration, multiple successive layers of regularly shaped shots can be offset by a factor of a number smaller than the shot spacing, and which is not an integral multiple of the spacing, over four. Moreover, such multiple layers can be purely random such that there is no identifiable pattern. Such randomness or irregularity should be sufficient to prevent the superposition of optical waives, and thus, prevent constructive and destructive interference from taking place.

In the Examples and in the teachings provided in this specification, the spacing and number of cuts are provided by way of illustration and are not limiting. Thus, it is understood that the size of the cubes can vary from the 0.25 mm shown and can be from about 10 µm to about 2.5 mm. Similarly the spacing and number of shell cuts can vary from that shown in the Figures corresponding to the Examples 1 through 6. As few as one such shell cut to as many as about 100 may be used, with their spacing being either uniform or varied. Further the distance between the shell cuts and the cube cuts or second shell cuts can vary from that shown in these Figures. For the closer spaced cuts, as well as, for the larger number of cuts smaller spot sizes for the focused laser are preferred. For example, an optical system of F/# (i.e., the ratio of the focal length to the beam diameter) equals 1.5 can produce spot size on the order of 3 µm and a Rayleigh range equal to +/−10 µm at a wavelength of 1 µm, which can be utilized to create more shell cuts, such as for example about 100 shell cuts. Such a spot size can also be utilized for smaller size cubes, such as down to about 10 µm. Although the smaller size spots may also be used for the other combinations of cuts provided by these examples. By way of further illustration an optical system of F/# equals 4 can be used to create 10 to 20 shells.

For the shot patterns disclosed and taught in this specification, as well as, those incorporated herein by reference, it may be advantageous for the outer most dimension of the shot pattern to avoid living tissue in the lens.

In the lens of an eye there is located an Organelle rich zone which is located in the fiber elongating region of the lens. In this region the fiber cells have a complete complement of organelles, including a cell nucleus. For example, in an approximately 50 year old lens the organelle rich region would about 250 μm from the equator tapering to about 100-150 μm at the poles (about 100 μm at the anterior pole and about 150 μm at the posterior pole).

Moving inward from the outer surface of the lens, there is a region having less organelles, which is referred to as the organelle degradation region. This region overlaps to some extent with the inner portion of the organelle rich zone. In this zone the organelles are being degraded or eliminated. The fibers are actively eliminating the organelles including the nucleus. For example, in an approximately 50 year old lens the degradation region would extend from the organelle rich zone to about 300 μm from the equator tapering to about 125-200 μm at the poles (about 125 μm at the anterior pole and about 200 μm at the posterior pole).

Moving inward from the outer surface of the lens, there is a region having essentially no organelles, which is refereed to as the organelle free zone. This region would be located inward of the degradation region and would overlap with this region to some extent. The fibers in the organelle free region would be denucleated and the material in this region of the lens would be considered denucleated.

The laser shot pattern can be such that no shots, or at a minimum essentially no shots, are place in the organelle rich zone. Further the shot pattern can be such that no shots, or at a minimum essentially no shots, are placed on the organelle degradation zone. Thus, as one way to avoid directing the laser to the living tissue of a lens it is provided by way of example that the shot pattern should be about a 0.4 mm or greater inset away from all the outer surfaces of the lens. Thus, by way of example, the laser pulses so directed would be on lens material that is denucleated. By way of further example the shot pattern should be restricted to a region that is inset about 0.3 mm from the surface at equator tapering to an inset that is about 0.125 mm at the surface by the anterior pole and an inset that is about 0.2 mm from the surface at the posterior pole.

A further parameter in obtaining optimal performance of the laser and laser shot pattern can be obtained by using the laser to provide very fast multiple pluses, in effect, a rapid burst of pulses to essentially on spot in the pattern. This implementation provides the dual advantages of reduced Rayleigh ranges through the use of lower energy pulses, while also increasing the probability of achieving photodisruption, which has also been referred to as Laser Induced Optical Breakdown (LIOB). Previously, it is believed that the ability to reduced Rayleigh range effects through lower energy pulses resulted in a decrease of the probability of achieving LIOB.

For example, a laser such as the Lumera Rapid Laser oscillator/amplifier can provide either one pulse of 20 μJ at a 50 kHz rate or a series of, or burst of, 2 to 20 pulses, with each pulse in the burst being separated by 20 nanoseconds, due to the 50 MHz laser oscillator. Thus, the burst can be delivered such that the total energy in the burst is approximately 20 μJ. For example, a burst of 4 pulses would have approximately 5 μJ per pulse and the rate at which each burst occurs would be 50 kHz.

Figure 22:
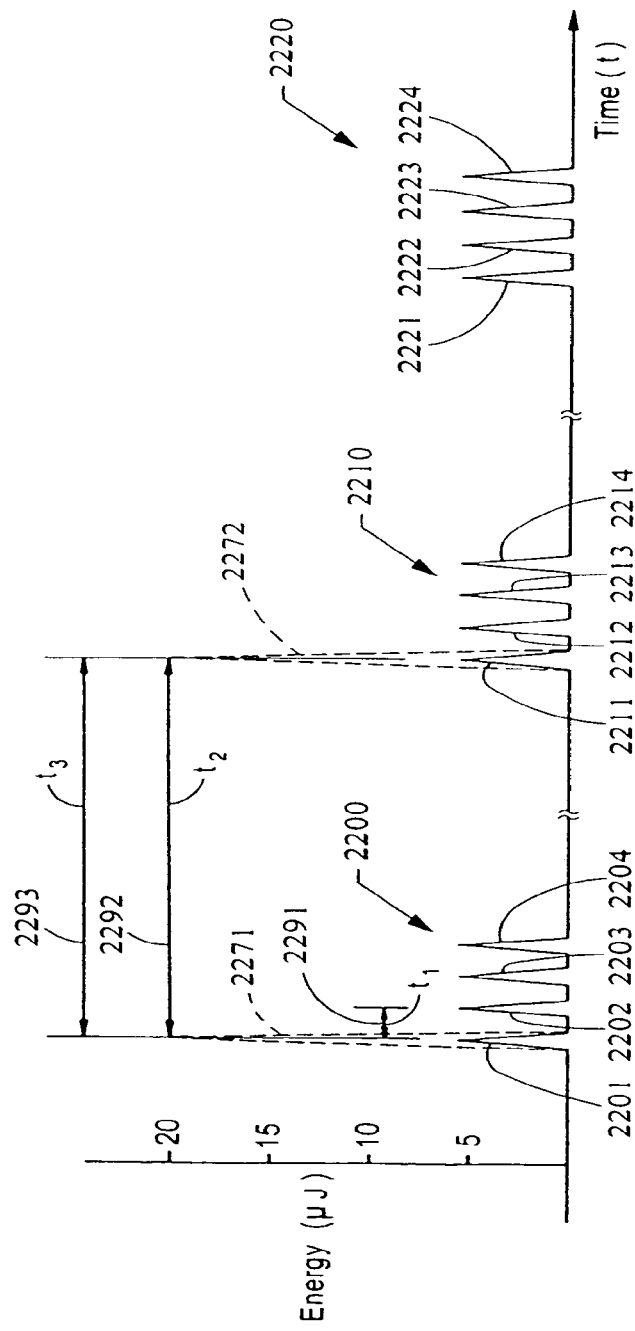
FIG. 22 is a drawing of laser pulses and bursts.

Referring to FIG. 22 there is provided an illustration that shows a comparison of single higher energy laser pulse with bursts of lower energy laser pulses over time. Accordingly, there is provided a single laser pulse 2271 (shown in dashed lines for illustration purposes only) having an energy of 20 μJ and another singe laser pulse 2272 (shown in dashed lines for illustration purposes only) having an energy of 20 μJ. The time shown by arrow 2292 between pulse 2271 and pulse 2272 is $t_2$. Thus, 2271 and 2272 represent the use of single 20 μJ pulses. If for example $t_2$ is equal to 20 u sec (micro seconds) then the rate for these pulses would be 50 kHz.

Still referring to FIG. 22 there is additionally shown burst 2200, 2210 and 2220. These burst are each shown as being made up of four laser pulses. The use of four pulses is solely for the purposes of illustration and is not meant to be and does not limit the amount of pulses that may be utilized. Thus, burst 2200 is made up of pulses 2201, 2202, 2203, and 2204; burst 2210 is made up of pulses 2211, 2212, 2213 and 2214; and, burst 2220 is made up of pulses 2221, 2222, 2223 and 2224. Each of the pulses in bursts 2200, 2210 and 2220 is 5 μJ. The time shown by arrow 2291 is the time between each individual pulse, e.g., 2201 and 2202, in a burst, e.g., 2200 and is referred to herein as $t_1$. The time shown by arrow 2293 between the first pulses in sequential bursts, e.g., 2201 and 2211, is $t_3$.

By way of example and for the purposes of illustration, it is provided that for a scan rate of about 30 kHz to about 200 kHz, a $t_3$ of about 5 μseconds to about 33 μseconds, and a $t_1$ of about 5 nanoseconds to about 20 nanosecond may be utilized.

For a given optical spot size, the amount of energy required to exceed photodisruption threshold might be 5 μJ. Rather then providing a single pulse of 20 μJ to a spot in a shot pattern, a burst of 4, 5 μJ pulses could be utilized, with each pulse in the burst being separated by about 20 nanoseconds. The use of such a burst will tend to increase the probability of achieving photodisruption threshold while also minimizing the Rayleigh range effects of extending the tissue effect in the z direction, or along the beam path. In this way the use of such bursts increase the probability of achieving photodisruption, which has also been referred to as Laser Induced Optical Breakdown (LIOB).

Accordingly, it is desirable to use energy densities in the region around LIOB threshold, i.e., the threshold at which photodisruption takes place, to minimize Rayleigh range effects. However, in the vicinity of LIOB threshold small and sometimes random variations in transmission, absorption, laser energy fluctuations, or optical spot size variations due to for example optical aberrations, can prevent LIOB in an undesirable and random matter throughout the treatment field. Optical spot size variations due to for example optical aberrations are especially found in low F/# systems.

It is further desirable to have complete treatment in any given treatment field. Thus, for example, in the shot patterns provided herein the treatment filed would be all of the x y and z coordinates of the pattern. It is further, for particular applications and in particular horizontal cuts, desirable to have laser energy densities in the vicinity of LIOB. Such energy densities minimize Rayleigh range effects and thus minimize the about of material in the z direction that is removed. However, by using such energy densities, and thus, obtaining the benefit of minimized Rayleigh range effects, the undesirable and random prevention of LIOB, as discussed above in the preceding paragraph, can occur. Thus, to minimize Rayleigh range effect and avoid LIOB prevention, it is provided to use of a burst of closely spaced in time pulses, wherein each pulse within the burst is in the vicinity of LIOB threshold. Through the use of such bursts the probability of achieving LIOB threshold is increased compared to using a single pulse with the same energy density.

Various other shot patterns are disclosed in greater detail in the specifications incorporated herein by reference, and include such configurations as cut horizontal partial planes whose extent is defined by a refractive shape. It is to be understood that as an alternative to horizontal planes, vertical partial planes or other orientation cuts whose extent is defined by the refractive shape may be used. Methods and shot patterns for treating and removal of cataracts and/or for clear lens extractions may be employed. Thus, there is provided a method for the structural modification of the lens material to make it easier to remove while potentially increasing the safety of the procedure by eliminating the high frequency ultrasonic energy used in Phaco emulsification today. In general, the use of photodissruption cutting in a specific shape patterns is utilized to carve up the lens material into tiny cube like structures small enough to be aspirated away with 1 to 2 mm sized aspiration needles.

Moreover, a shot pattern to create 0.5 mm sized cubes out of the lens material following the structural shape of a 45-year old Burd Model lens may also be utilized. Thus, there is provided a shot pattern that creates grid like cuts, the end of which cuts essentially follows the shape of the lens. The sequence of laser shots in this pattern may be executed from posterior to anterior, as in most of the patterns disclosed herein, to obtain more predictable results by reducing the variation caused by shooting through gas bubbles. However, it may be desirable to shoot cataracts from the anterior to the posterior for the purpose of choosing the lesser of two undesirable effects. Thus, it may be advantageous to shoot through the gas bubbles, or let them dissipate, rather then shooting through cataractus tissue, which much more severely scatters the light and more quickly prevents photodissruption compared to gas bubble interference. Accordingly, it is proposed to photodissrupt the most anterior sections of the cataract first, then move posteriorly, shooting through gas bubble remnants of cataractous tissue, to the next layer of cataract tissue below. In addition to shooting the laser in anterior z planes then moving posterior, it is further provided to essentially drill down anterior to posterior, which we call the z axis throughout this document and then move in x/y and drill down again.

Additionally, shot patterns that relate to gradient index modification of the lens may be employed. Thus, it is provided to use the photodissruptive laser in the creation of small voids within the lens fiber material which will then fill-in with aqueous humor fluid which has a lower index of refraction and, via area weighting or volume weighting, decrease the net refractive index of a particular region. Accordingly, if different void densities are placed in nested shell volumes, then this would diminish the average index of refraction of essentially concentric regions in a similar manner to the youthful lens. Further, a gradient index modification, which has different void densities placed in nested volumes, may be employed. Thus, there is provided a series of nested shot patterns with each pattern creating an incrementally different void density in the lens material. For example, if a nominal 25% weighting efficiency was obtained in the most densely treated region, filling that volume with 1.38 index of aqueous humor, and the remaining region that was 75% lens material of index 1.42, then the average resultant index of refraction would be 0.25*1.38+0.75*1.42 or 1.41, which we see from FIG. 31, that would restore the gradient from the center to a 2 mm radius, which is most central optical region for visual function. Thus, a distributed regional treatment of increasing density from the center of the lens to the periphery of the lens may be employed.

Shell patterns may also be employed that provide for cutting in relation to suture lines. Thus, cuts along either modeled suture lines, or measured suture lines may be used. The latter being provided by the measuring of patient lens sutures with a CCD camera and aligning suture cuts to the measured locations of suture lines. Thus, the brightest suture lines and or those with the widest spatial distribution likely belong to the deepest layers, and perhaps the initial Y suture branches found in the fetal nucleus. Further, there it is provided to cut Y suture shapes at the lowest layers in the lens and then increasing the number of cuts as the layers move out peripherally.

Further, sectional patterns may be employed. Such patterns would include the cube patterns, variations in the shape and size of this cube pattern, concentric cylinders, radial planes, horizontal planes and vertical planes, partial shells and shells, and combinations thereof. As used to describe these patterns, vertical refers to essentially parallel to the optical axis, i.e., the AP axis. These sectional patterns are employed within, or to comprise, a particular shaped volume. Thus, these sectional patterns can be used in shaped volumes that provide for positive or negative refractive corrections. Further, these shaped patterns can be used in shaped volumes that result in shaped structural weakening, which causes shape change and results in a positive or negative refractive correction. Additionally, shaped structural weakening may also result in increased accommodative amplitude.

Moreover, these patterns can be employed in conjunction with each other, i.e., vertical and horizontal, or in isolation, i.e., only vertical or horizontal, at various locations in the lens, which locations can range from totally separate, to slightly overlapping, to overlapping. Additionally, by selectively arranging placement and density of these patterns and/or combination of primarily vertical and primarily horizontal patterns, local structure in the lens can be weakened by varying and predetermined amounts, which can result in selective flexibility and shape changes. Thus, through such selective placement and density determinations shaped structural weakening may be accomplished.

These sectional patterns may be employed using primarily vertical or primarily horizontal patterns. Primarily vertical patterns, which include vertical cylinders and vertical planes, may provide more complete cleaving than essentially horizontal patterns due to the relative long depth of field of a photo disruption spot compared to the narrow width of the spot. Primarily horizontal patterns, such as horizontal planes and shell cuts near the center of the lens, i.e, poles, may provide lesser structural weakening due to less complete cleaving. Moreover, primarily horizontal patterns, such as shells cut to the shape of the lens, will tend to preserve the overall shape of the lens, while still providing some structural weakening to improve flexibility.

In determining the particular types of structural patterns to use, greater structural weakening with less regard to preserving initial shape may be employed by providing primarily vertical patterns therein. Moreover still greater structural weakening with less regard to preserving initial shape may be employed by providing both primarily vertical and primarily horizontal patterns therein. Further, in determining the particular types of structural patterns to use, greater structural weakening with less regard to preserving initial shape may be employed within the center of the lens, such as the compacted fetal nucleus by providing primarily vertical patterns therein. Moreover still greater structural weakening with less regard to preserving initial shape may be employed within the center of the lens, such as the compacted fetal nucleus by providing both primarily vertical and primarily horizontal patterns therein.

Optical performance and optical quality are dependent upon the surface shape and quality of the lens. Thus, to balance increasing accommodative amplitude via increased flexibility with maintaining and/or obtaining lens shape for desired optical performance and optical quality various combinations, densities and placements of these patterns may be employed. By way of illustration, a combination of central patterns and peripheral patterns may be utilized to maximize structural weakening and control of lens shape. Thus, patterns can be selected for placement in the center of the lens, such as the fetal and embryonic nucleus, which will result in maximum shaped structural weakening with minimal effect on lens surface shape changes, which surface effect is based essentially upon the placement of the pattern. In conjunction with this central pattern more peripheral lens areas, such as the infantile, adolescent and adult nucleus and cortex, may be treated with primarily horizontal patterns to increase flexibility yet maintain the shape of the lens. Moreover, these primarily horizontal patterns may be selected such as to change the lens surface shape in a predetermined manner.

Additionally, the forgoing methods for increasing accommodative amplitude, as well as other such methods, may result in an increase in refractive error. Thus, as the accommodative amplitude is increased by a diopters range, a refractive error may be introduced into the lens, hereinafter referred to as an induced refractive error. This induced refractive error can be predicted and/or observed. This induced refractive error can be reduced, prevented, and/or minimized by the predetermined placement of additional laser shots, either as part of the shot pattern for increasing accommodative amplitude or as a separate shot pattern. Additionally, this induced refractive error can be addressed by any technique for correcting refractive error known to those skilled in the art.

Generally, to correct for, prevent and/or minimize the effect of induced refractive error, after a laser procedure to increase accommodative amplitude, shots are selected for the shot pattern to simultaneous correct refractive error while increasing accommodative amplitude. Further, these selected shots may provide shaped structural weakening for the purpose of refractive error change. Thus, these selected shots to correct induced refractive error include modifications to the shape of the pattern, modifications to the placement of the shots, and may further include the same number of shots or a higher or lower number of shots. For determining the selected shots the induced refractive error can be predicted, based upon modeling and/or prior testing and observation.

Although less preferred, after the laser procedure to increase accommodative amplitude is preformed, the actual change in refraction of the eye may be determined through observation. Based upon this observed change in refraction a corrective refractive procedure is selected to correct and/or minimize the observed change. This corrective refractive procedure may be a laser shot pattern provided to the lens, such as but not limited to the refractive laser shot patterns provided herein. This corrective refractive procedure may also be laser corrective procedure that is directed towards the cornea, such as laser techniques known to those skilled in the art for treating refractive errors through modification of corneal tissues, such as PRK and LASIK. In these corneal procedures the laser for correcting induced refractive error may be different from the laser used for the accommodative amplitude procedure. Additional corneal refractive procedures are known to those of skill in the art and may be employed to address induced refractive error; such procedures included but are not limited to radial keratotomy and conductive keretoplasty. Moreover, the observed change in refraction may be addressed by spectacles and/or contact lens.

The corrective refractive procedure may be performed shortly after the procedure to increase accommodative amplitude. However, the corrective refractive procedure may also be provided at longer periods of time after the accommodative amplitude procedure, including, days, weeks, months or longer.

The correction of induced refractive error may be further understood by the following by the following illustrative and exemplary teaching. Prior to lens flexibility treatment, the patient's range of accommodation, will extend about a corrected distance vision of 0 diopters. After lens flexibility treatment, the patient's range of accommodation will be substantially increased but the range will now extend negatively from 0 to $-\beta$ diopters. A second lens refractive treatment is performed to shift the range positively by adding $\beta$ diopters of refractive power to the lens. In this way the range of the patient's accommodation extends positively from 0 to $\beta$ diopters In any given patient population the flexibility power change will not be $-\beta$ but instead will be distributed about a mean $X_{flex}$ (which we design to be $-\beta$) with a variance of $\sigma^2_{flex}$. Similarly, the refractive power change will also not be $\beta$ but will be distributed about a mean $X_{ref}$ (which we design to be $\beta$) with a variance of $\sigma^2_{ref}$. The outcome of the sum of both the flexibility and refractive power change will also be distributed about a mean of $X_{flex}+X_{ref}=0$ with a total standard deviation of $sd_{total}=\text{sqrt}(\sigma^2_{flex}+\sigma^2_{ref})$ for normally distributed populations.

While it is desired that the sum of the flexibility power change and the refractive power change be 0, the normal range of these power changes will result in some of the patients experiencing a range of accommodation that will extend not from 0 but from some positive value. This shift would be undesirable as it would require additional refractive correction to restore the patients nominal distance vision. These patients are in the population of patients whose total flexibility and refractive power change is greater than the mean value of 0. By shifting this distribution negatively away from 0 we can reduce the percentage of patients needing further refractive correction.

To prevent the need for extra refractive correction, the magnitude of the refractive power cut is reduced from $X_{ref}$ to $X_{ref}-\alpha \times sd_{total}$ where $\alpha=1$ results in 16%, $\alpha=2$ results in 2.5%, and $\alpha=3$ results in 0.15% of the patients experiencing accommodation ranges extending not from 0 but from some positive value for normally distributed populations. This approach minimizes the need for additional refractive correction by reducing the range of accommodation from $\beta$ to $\beta-\alpha \times sd_{total}$.

The components and their association to one another for systems that can perform, in whole or in part, these examples are set forth above in detail. Additionally, it is noted that the functions of the methods and systems disclosed herein may be performed by a single device or by several devices in association with each other. Accordingly, based upon these teachings a system for performing these examples, or parts of these examples, may include by way of illustration and without limitation a laser, an optical system for delivering the laser beam, a scanner, a camera, an illumination source, and an applanator which has reference marks thereon. These components are positioned so that when the eye is illuminated by the illumination source, light will travel from the eye through the applanator to the scanner. In this system the illumination source is movable with respect to the eye to provide varying angles by which the eye can be illuminated.

Similarly, such system may also include by way of example and without limitation a laser, a system for determining the position and shape of components of an eye, a camera, a controller (which term refers to and includes without limitation processors, microprocessors and/or other such types of computing devices that are known to those of skill in the art to have the capabilities necessary to operate such a system), an illumination source, and an eye interface device. In this system the scanner is optically associated with the eye interface device, such that when the eye is illuminated by the illumination source, light will travel from the eye through the eye interface device to the scanner. The scanner is further optically associated with the camera, such that the scanner has the capability to provide stereo pairs of images of the eye to the camera. The camera is associated with the controller and is capable of providing digital images of the eye to the controller; and, the controller further has the capability to determine, based in part upon the digital images provided from the camera, the shape, position and orientation of components of the eye.

Moreover, such systems may also include by way of example and without limitation a system for delivering a laser to an eye. This system would have a laser, a scanner, a camera, an illumination source, an eye interface device, a means for determining the shape and position of components within an eye and a means for directing the delivery of a laser beam from the laser to a precise three dimensional coordinate with respect to the components of the eye, the means for directing the delivery of the laser beam having the capability to direct the beam based at least in part on the determination of the shape and position of components within the eye by the determining means.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. A system for delivering a laser beam to a lens of an eye in a plurality of patterns comprising:
    a) a laser;
    b) an optical path for directing a laser beam from the laser to the lens of the eye;
    c) a control system configured to direct the laser beam in a first pattern on a first portion of the lens of the eye; and, to direct the laser beam in a second pattern on a second portion of the lens of the eye;
        i) wherein the second pattern is configured to cut the lens into volumetric shapes;
        ii) wherein the first pattern is configured to create an opening in the lens capsule for removal of the volumetric shapes; and,
    e) a 3-dimensional viewing apparatus, whereby the system is configured to provide a stereoscopic image of the lens.

2. The system of claim 1, wherein the second pattern is cubic.
3. The system of claim 1, wherein the second shot pattern comprises a plurality of nested shells.
4. The system of claim 1, wherein the second shot pattern comprises a vertical cut that is parallel with an optical axis of the eye.
5. The system of claim 1, wherein the second shot pattern comprises an annular cut that is parallel with an optical axis of the eye.
6. The systems of claims 1, wherein the 3-dimensional viewing apparatus comprises only a single ccd camera.
7. The systems of claims 2, wherein the 3-dimensional viewing apparatus comprises only a single ccd camera.
8. The systems of claims 3, wherein the 3-dimensional viewing apparatus comprises only a single ccd camera.
9. The systems of claims 4, wherein the 3-dimensional viewing apparatus comprises only a single ccd camera.
10. The systems of claims 5, wherein the 3-dimensional viewing apparatus comprises only a single ccd camera.
11. The system of claim 1, wherein the 3-dimensional viewing apparatus is configured to send 3-dimensional information to the control system.
12. The system of claim 11, wherein the 3-dimensional information is a stereoscopic image.
13. The system of claim 11, wherein the control system is configured to use the 3-dimensional information to determine the shape of the lens.
14. The system of claim 11, wherein the control system is configured to use the 3-dimensional information to determine the laser shot placement.
15. The system of claim 11, wherein the control system is configured to use the 3-dimensional information to determine the laser shot pattern.
16. A system for delivering a laser beam to a lens of an eye in a plurality of patterns comprising:
    a) a laser;
    b) an optical path for directing a laser beam from the laser to the lens of the eye;
    c) a control system configured to direct the laser beam in a first pattern on a first portion of the lens of the eye; and, to direct the laser beam in a second pattern on a second portion of the lens of the eye;
        i) wherein the second pattern is configured to cut the lens into volumetric shapes;
        ii) wherein the first pattern is configured to create an opening in the lens capsule for removal of the volumetric shapes; and,
    e) a 3-dimensional viewing apparatus, whereby the system is configured to provide 3-dimensional information about the lens to the control system.
17. The system of claim 16, wherein the 3-dimensional information is a stereoscopic image.
18. The system of claim 16, wherein the control system is configured to use the 3-dimensional information to determine the shape of the lens.
19. The system of claim 16, wherein the control system is configured to use the 3-dimensional information to determine the laser shot placement.
20. The system of claim 16, wherein the control system is configured to use the 3-dimensional information to determine the laser shot pattern.

* * * * *